US011626202B2

(12) United States Patent
deHaan et al.

(10) Patent No.: US 11,626,202 B2
(45) Date of Patent: Apr. 11, 2023

(54) MEDICAL TESTING APPARATUS

(71) Applicants:Jordan Jacek deHaan, Denver, CO (US); William Jackson Bowen, III, Denver, CO (US)

(72) Inventors: Jordan Jacek deHaan, Denver, CO (US); William Jackson Bowen, III, Denver, CO (US)

(*) Notice: Subject to any disclaimer, the term of this patent is extended or adjusted under 35 U.S.C. 154(b) by 0 days.

(21) Appl. No.: 17/825,738

(22) Filed: May 26, 2022

(65) Prior Publication Data

US 2022/0285007 A1    Sep. 8, 2022

Related U.S. Application Data

(63) Continuation-in-part of application No. 17/149,157, filed on Jan. 14, 2021.

(60) Provisional application No. 62/962,885, filed on Jan. 17, 2020, provisional application No. 63/092,441, filed on Oct. 15, 2020.

(51) Int. Cl.
*G16H 30/20* (2018.01)
*B01L 9/00* (2006.01)
*G06V 40/16* (2022.01)
*G01N 21/88* (2006.01)

(52) U.S. Cl.
CPC .............. *G16H 30/20* (2018.01); *B01L 9/527* (2013.01); *G01N 21/8851* (2013.01); *G06V 40/172* (2022.01); *B01L 2300/023* (2013.01); *B01L 2300/0609* (2013.01)

(58) Field of Classification Search
CPC .......... A61P 43/00; A61P 35/00; A61P 31/16; A61P 31/04; A61P 3/04; A61P 25/00; A61P 3/10; A61P 31/10; A61P 9/04; A61B 10/0045; A61B 5/14532; A61B 5/14539; A61B 2010/008; A61B 5/14514; A61B 5/1455; A61B 5/150358; G01N 33/56983; G01N 33/6893; G01N 35/04; G01N 2469/20; G01N 35/025; G01N 35/0099; G01N 1/38
See application file for complete search history.

(56) References Cited

U.S. PATENT DOCUMENTS

| 2010/0285490 A1* | 11/2010 | Dees | G01N 33/54373 |
| | | | 435/7.1 |
| 2015/0353919 A1* | 12/2015 | Mielke | B01L 3/5029 |
| | | | 435/6.12 |
| 2020/0303044 A1* | 9/2020 | Stephen | G16H 10/40 |

* cited by examiner

*Primary Examiner* — Alex Kok S Liew
(74) *Attorney, Agent, or Firm* — Roger A. Jackson

(57) ABSTRACT

A medical testing apparatus for a user to help to authenticate and track the process of a test kit that is received into the medical test apparatus, the test kit includes components of an extended nasal/oral swab, a buffer tube, a reagent disposed within the buffer tube, a nozzle cap, and a test card, the kit is for testing for a presence or a non-presence of an infection that utilizes an internet connected electronic device with a camera for communication to third parties. The apparatus includes a test stand that is configured to partially receive the electronic device and to partially receive the test kit in a positional alignment to for the camera to record an unique identification code for each test kit component, and for the camera user facial recognition, further the test stand camera records infection status.

14 Claims, 20 Drawing Sheets

MEDICAL TESTING APPARATUS

RELATED PATENT APPLICATIONS

This application is a continuation in part of U.S. patent application Ser. No. 17/149,157 filed on Jan. 14, 2021 by Jordan Jacek de Haan of Denver, Colo., U.S., William Jackson Bowen III of Denver, Colo., U.S., William George Norman Coon of Longmont, Colo., U.S., and Shane Kawika Vogt of Lafayette, Colo., U.S., that claims the benefit of U.S. provisional patent application Ser. No. 62/962,885 filed on Jan. 17, 2020 by Jordan Jacek de Haan of Denver, Colo., U.S. and William Jackson Bowen III of Boulder Colo., U.S., and also claims the benefit of U.S. provisional patent application Ser. No. 63/092,441 filed on Oct. 15, 2020 by Jordan Jacek de Haan of Denver, Colo., U.S., William Jackson Bowen III of Denver, Colo., U.S., William George Norman Coon of Longmont, Colo., U.S., and Shane Kawika Vogt of Lafayette, Colo., U.S.

TECHNICAL FIELD

The overall field of this invention generally pertains to the field of molecular diagnostics, in particular to a portable self-authenticating point-of-collection diagnostic system, method, and components enabled to connect with a smart device accessory for tracking results and remotely sending data to an authorized third party.

BACKGROUND OF INVENTION

COVID testing is of paramount importance both for availability and authentication being compounded by the fact that the COVID testing needs to be done on a recurring basis over time for an individual. The typical access to COVID test usually requires a visit to a testing site that can be inconvenient and involve significant waits in line being very frustrating for an individual to go through, plus add to the fact that this testing ordeal must be done again and again further compounds the individuals frustration with current COVID testing protocol.

The current FDA approved COVID tests are the RT-PCR test or as termed the molecular test and the Antigen test.

The RT-PCR test works by detecting genetic material of the virus using a lab technique called reverse transcription polymerase chain reaction hence, "RT-PCR". The test is accomplished by collecting a fluid sample via inserting a long nasal swab and taking fluid from the back of the nose or by taking a sample from the back of the throat, or even saliva and/or sputum can be used via spitting into a tube. Results can be in minutes if analyzed at the test site or in days if sent to an outside lab, wherein the outside lab test is more accurate that the on-site test.

The Antigen test detects certain proteins in the virus, again using a nasal swab to get a fluid sample and some antigen tests produce results in minutes otherwise an outside lab can be used for results.

If a positive result is shown in the Antigen test or even a negative-wherein there can be false negatives the RT-PCR test can be used to confirm results.

Current COVID testing protocol typically requires testing when;
1. COVID symptoms exist
2. Close contact with someone who has COVID symptoms (could be workplaces, schools, various public places, certain travel-also can be before and/or after travel,
3. Medical professional recommends
4. Health care workers
5. First responders
6. Live in long-term care facilities
7. Hospitalized
8. Identified through contact tracing for being at risk of COVID
9. General demographic surveillance testing for specific data gathering
10. Certain preexisting health conditions
11. Higher risk demographics
12. Prior to attending high people density gatherings An obvious solution would be at home COVID testing which would more easily allow more frequent testing and have a high convenience factor by eliminating travel to testing centers and waiting in lines, plus reducing exposure to COVID to others at the testing centers. However, home testing has issues with accuracy and authenticity, being accuracy with the test result at individuals will not be as skilled with administering the test to themselves as a professional would be, plus problems with authenticity in verifying the individual who tested themselves that the includes time and date of the test. So, with all the advantages of home COVID testing, the challenges of accuracy and authenticity need to be overcome.

Currently the FDA has granted emergency use authorization (EUA) for certain at home COVID tests wherein the user collects nasal fluid of saliva and then send the sample to a remote lab to be analyzed-taking usually at least a few days, wherein some at home test kits facilitate at home results indication, thus skipping the send the sample to the lab step. In general, the Antigen tests are not considered as reliable as the RT-PCR tests, so as a proposal to further increase the accuracy of testing a user could of course double test to confirm the same result-wherein the repeated tests could be 1-2 days apart for higher negative test result confidence, or complete an Antigen test and then a RT-PCR test to confirm results from two different tests.

However, there are generally no ways to ensure that the individual using the test kit has not tampered with the test kit or the results unless the test is conducted by another individual such as a nurse, technician, or at a health care facility among others.

Ongoing and repeatable authentication of the home test is an issue also as the test result being verified with a particular user as the need for scheduled frequent testing that needs to be reported to airlines, schools, employers, government agencies, and other entities to determine if quarantine is needed and for a schedule for future testing after quarantine and for face mask use. Further authentication in testing is important for contact tracing plus determining the future testing schedule for a particular individual and potential quarantine schedules Authentication can include using the individual's smart phone through an application that can as a first step scan a particular test kit code to start a database that will be transmitted on-line to help in contact tracing and data surveillance, next a second step of verifying the smart phone user's identity through various user recognition technologies, for a third step the application will provide detailed test kit use instructions based on the test kit code. During the test the application will engage a fourth step of time, date, and place stamp recording of a video of the individual taking the test with further verifications of a match of the phone user's identity from step two and a verification of the test kit negative or positive result. Further instructions in a fifth step will be given depending upon if the test result is positive or negative. A sixth step will setup appropriate subsequent testing requirements via smart phone notifications.

If an outside lab is required to determine the negative or positive test kit result then the fourth step is expanded to include video recording of placing the test sample into the envelope and a fourth step addendum of scanning the envelope, further the fifth step is modified to be initiated by the outside lab entering the test result into the application cloud database.

Thus, there remains a need for a device that is easy to use, tamper-proof, and allows monitoring of an individual remotely while providing real time, documented test results to the requesting party. It is the object of the present invention to provide a device that allows monitoring a person under supervision without requiring in-person appointments. It is also the object of the present invention to provide a device that makes the person taking the test and being monitored to be accountable for themselves and also removes the person's ability to find a way to cheat their COVID test. It is also the object to provide real-time test results to a person that is requesting the information remotely.

The present disclosure recognizes the unsolved need for a low cost, easy to use, tamper-proof, remote supervised COVID testing, ease of sharing results remotely, and a more efficient way to digitize file, and store COVID test results. The test results can be automatically compiled in one place for more accurate surveillance COVID test data collection.

SUMMARY OF INVENTION

Broadly, the present invention is a medical testing apparatus for a user to help to authenticate and track the process of a separate test kit that is received partially into the medical test apparatus, wherein the test kit includes components of an extended nasal/oral swab, a buffer tube, a reagent disposed within the buffer tube, a nozzle cap, and a test card, the test kit is for testing to obtain a test result of a presence or a non-presence of an infection that utilizes an internet connected electronic device with a camera for communication of the authentication and tracking process to third parties. The medical testing apparatus includes a test stand that is sized and configured to partially receive the electronic device and to partially receive the test kit in a positional alignment to operationally facilitate the camera to more accurately record an unique identification code for each test kit component, and for the camera to identify user facial recognition, further the test stand records the test kit process steps using the camera including the presence or non-presence of the infection.

These and other objects of the present invention will become more readily appreciated and understood from a consideration of the following detailed description of the exemplary embodiments of the present invention when taken together with the accompanying drawings, in which;

BRIEF DESCRIPTION OF DRAWINGS

FIG. 19 shows cross section 19-19 from FIG. 15, wherein FIG. 19 shows the test card disposed within the shallow cavity that is in the base mount portion and utilizing the partial end extension, with all operational to position and support the test card for authentication via the camera as shown in FIG. 15, note that the deep cavity is also shown in relation to the shallow cavity with the first and second perimeters; and FIG. 20 shows view 20-20 from FIG. 2, wherein FIG. 20 shows the partial end extension along with the base mount portion and the deep cavity in relation to the shallow cavity with the first and second perimeters along with the shared perimeter that forms a part of the first and second perimeters.

REFERENCE NUMBERS IN DRAWINGS

Figure 4:
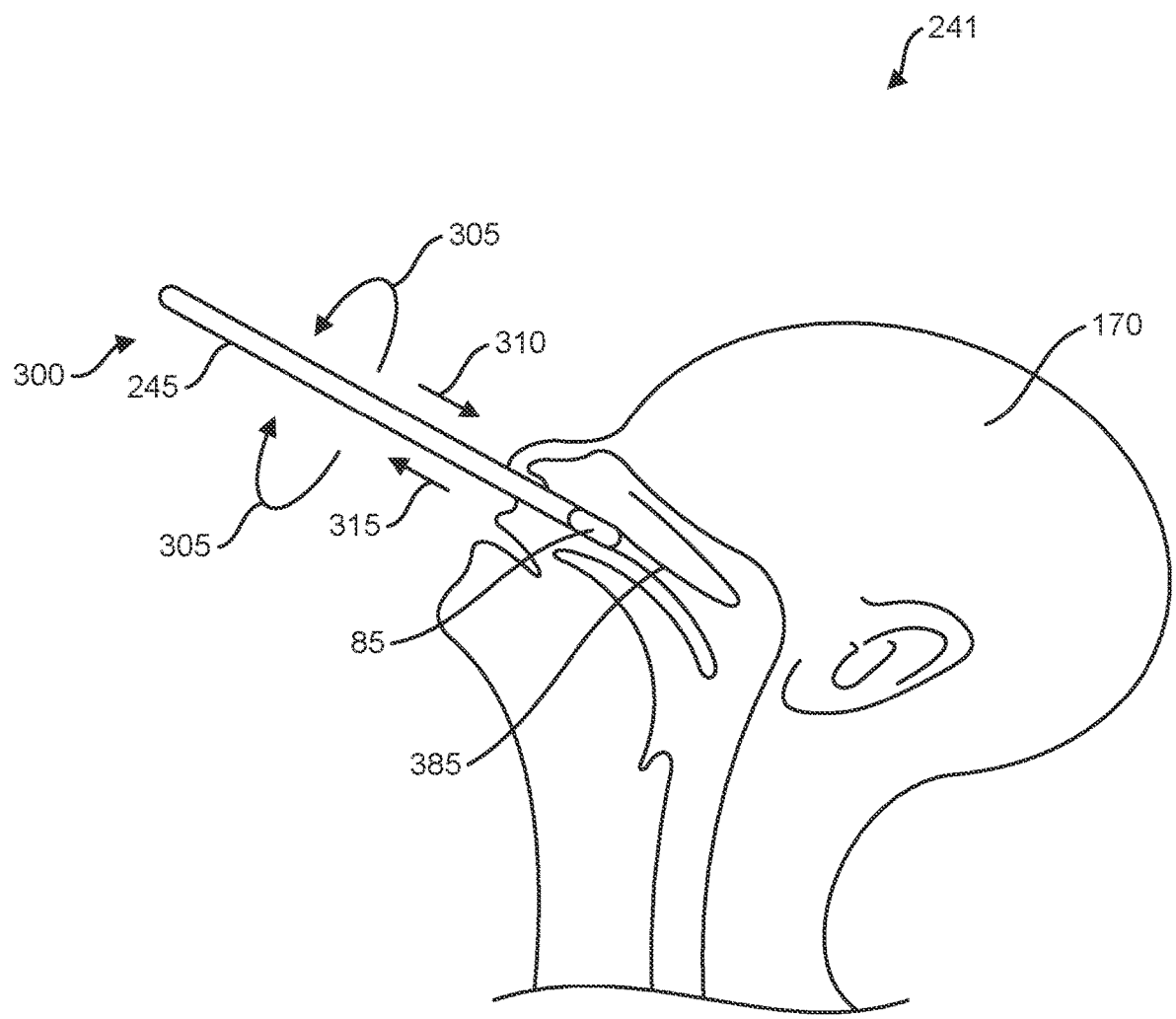
FIG. 4 shows a first step that includes a side elevation cross section view of a user with the nasal swab inserted into their nasal cavity with a rotational and insertion step/ removal step movement of the nasal swab in relation to the nasal cavity to obtain a proper nasal swab sample.
Figure 5:
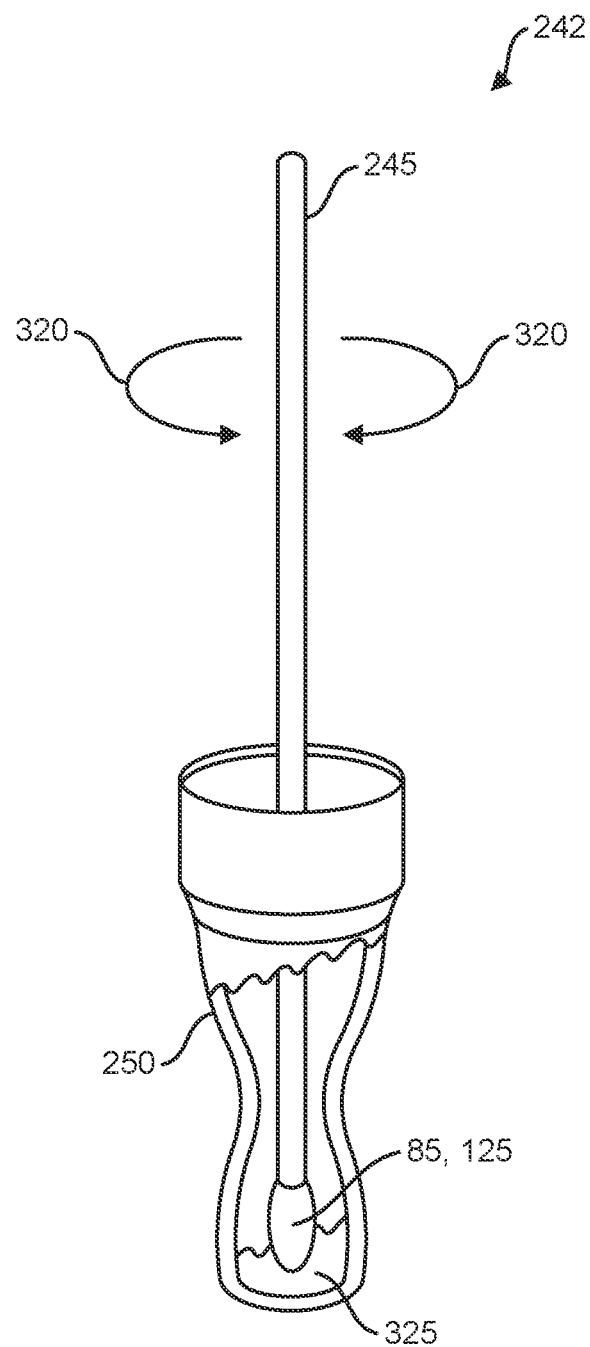
FIG. 5 shows a second step that includes an upper perspective view of the extraction buffer tube with the nasal swab inserted into a reagent fluid commensurating with a rotation step of the nasal swab in the reagent fluid.
Figure 6:
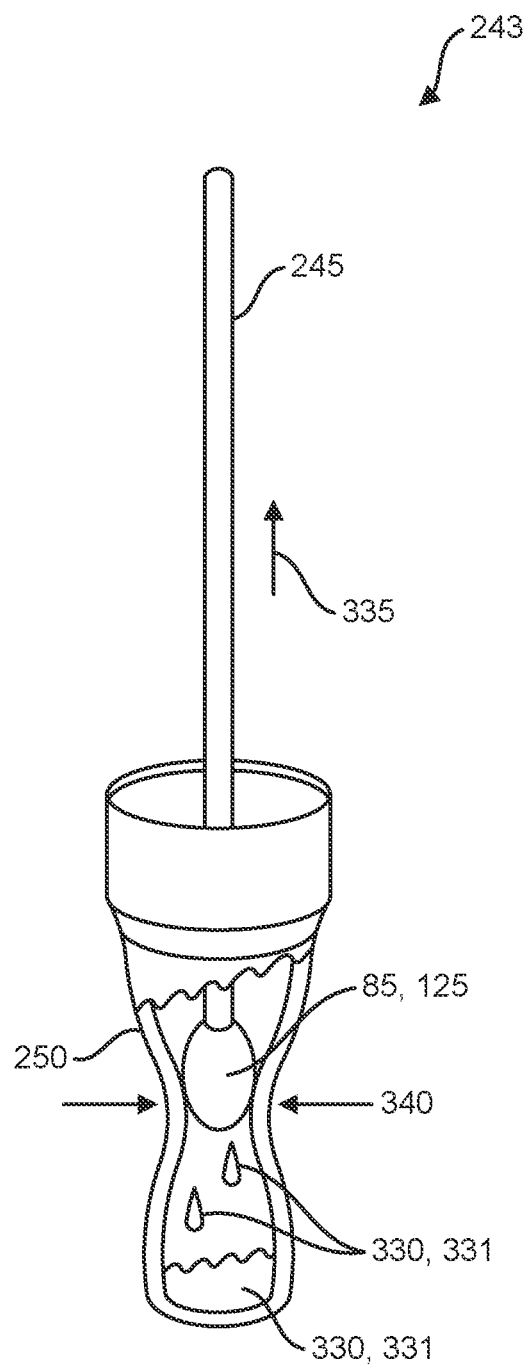
FIG. 6 shows a third step that includes an upper perspective view of the extraction buffer tube with the nasal swab with partial removal from the extraction buffer tube to squeegee the nasal swab from the reagent fluid via a compression step on the extraction buffer tube to place nasal secretions into the reagent fluid.
Figure 7:
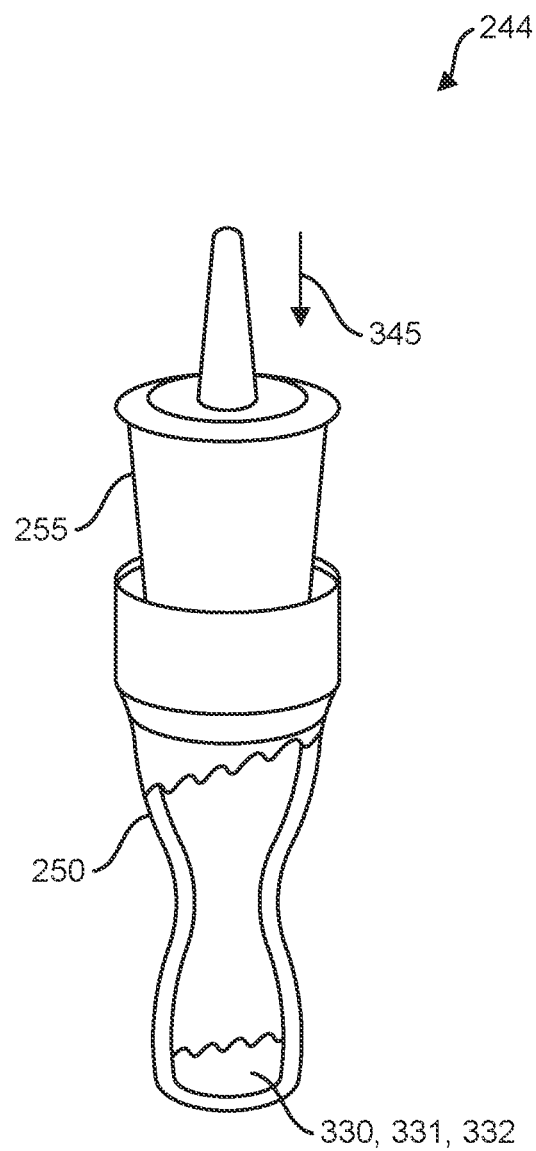
FIG. 7 shows a fourth step that includes an upper perspective view of the extraction buffer tube with the nozzle cap in a placing step into the extraction buffer tube with the reagent fluid that contains nasal secretions from the nasal swab.
Figure 10:
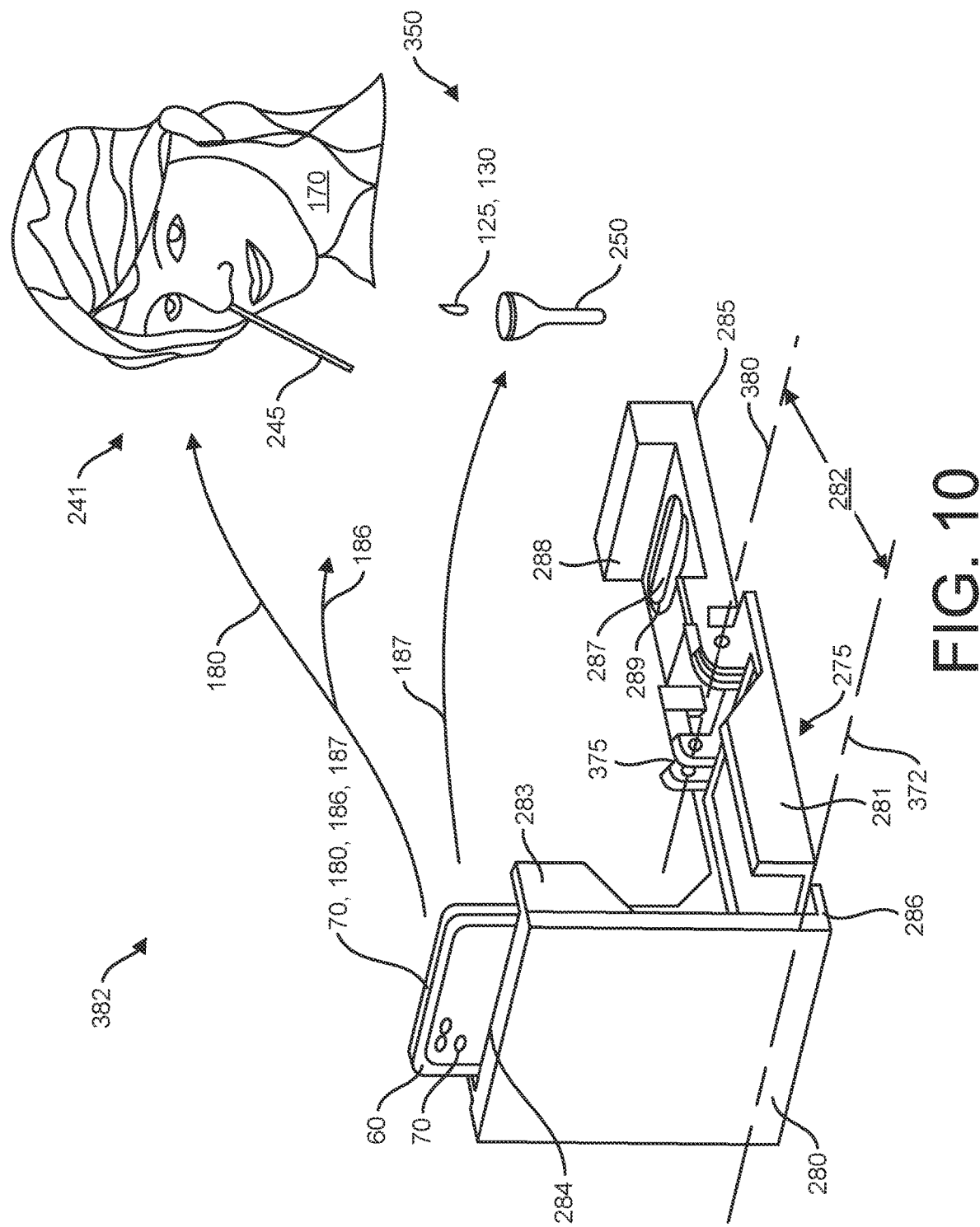
FIG. 10 shows the first step test authentication in an upper perspective view that shows the test stand that is in the second operational state being laid flat, wherein the electronic device is disposed in the left side of the stand with the electronic device including a camera facing to the right that is documenting the use of the nasal swab by the user, plus shown is the extraction buffer tube with saliva and sputum.
Figure 11:
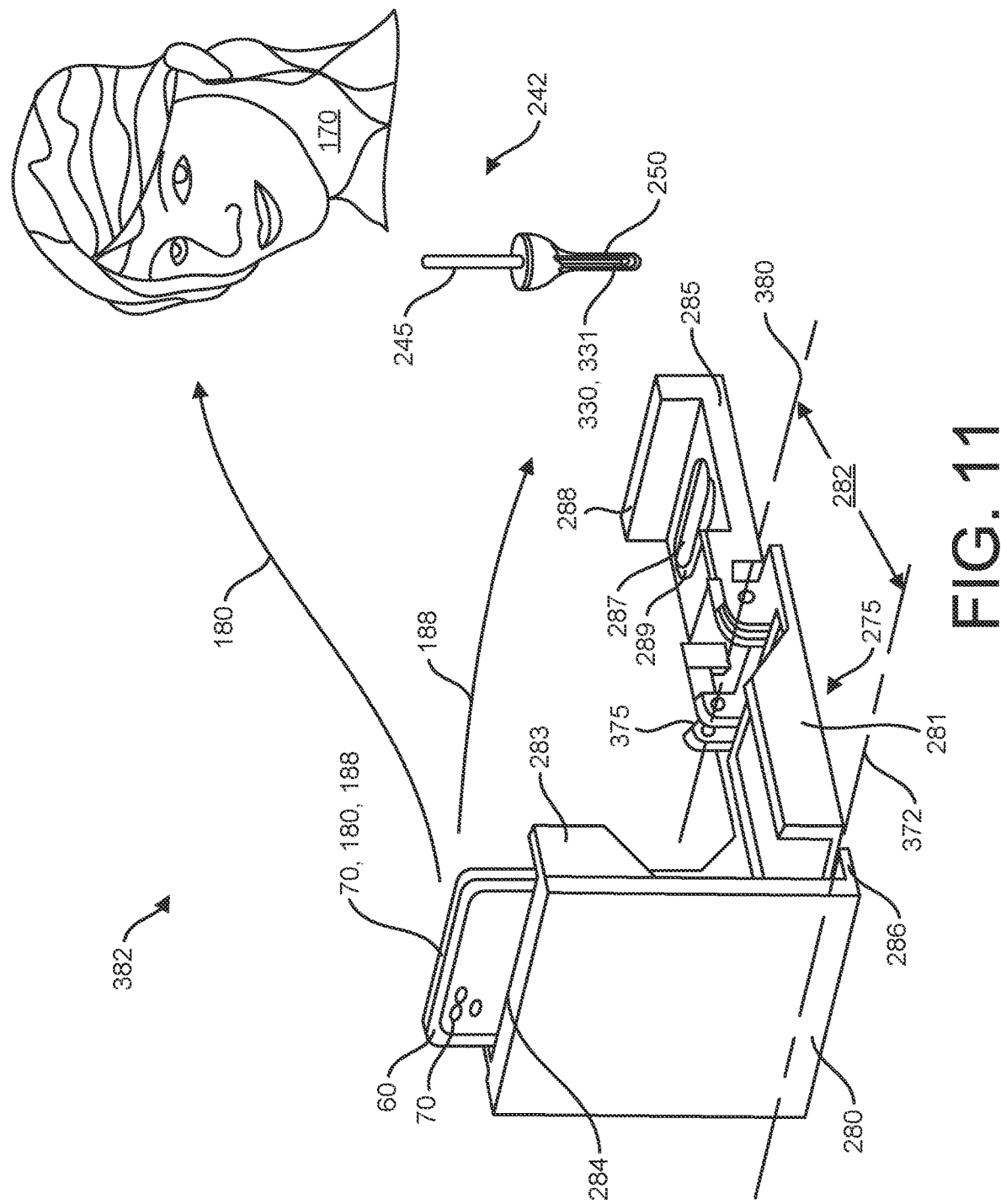
FIG. 11 shows the second step test authentication in the upper perspective view that shows the test stand that is in the second operational state being laid flat, wherein the electronic device is disposed in the left side of the stand with the electronic device including a camera facing to the right that is documenting the nasal swab inserted into the reagent fluid in the extraction buffer tube.
Figure 12:
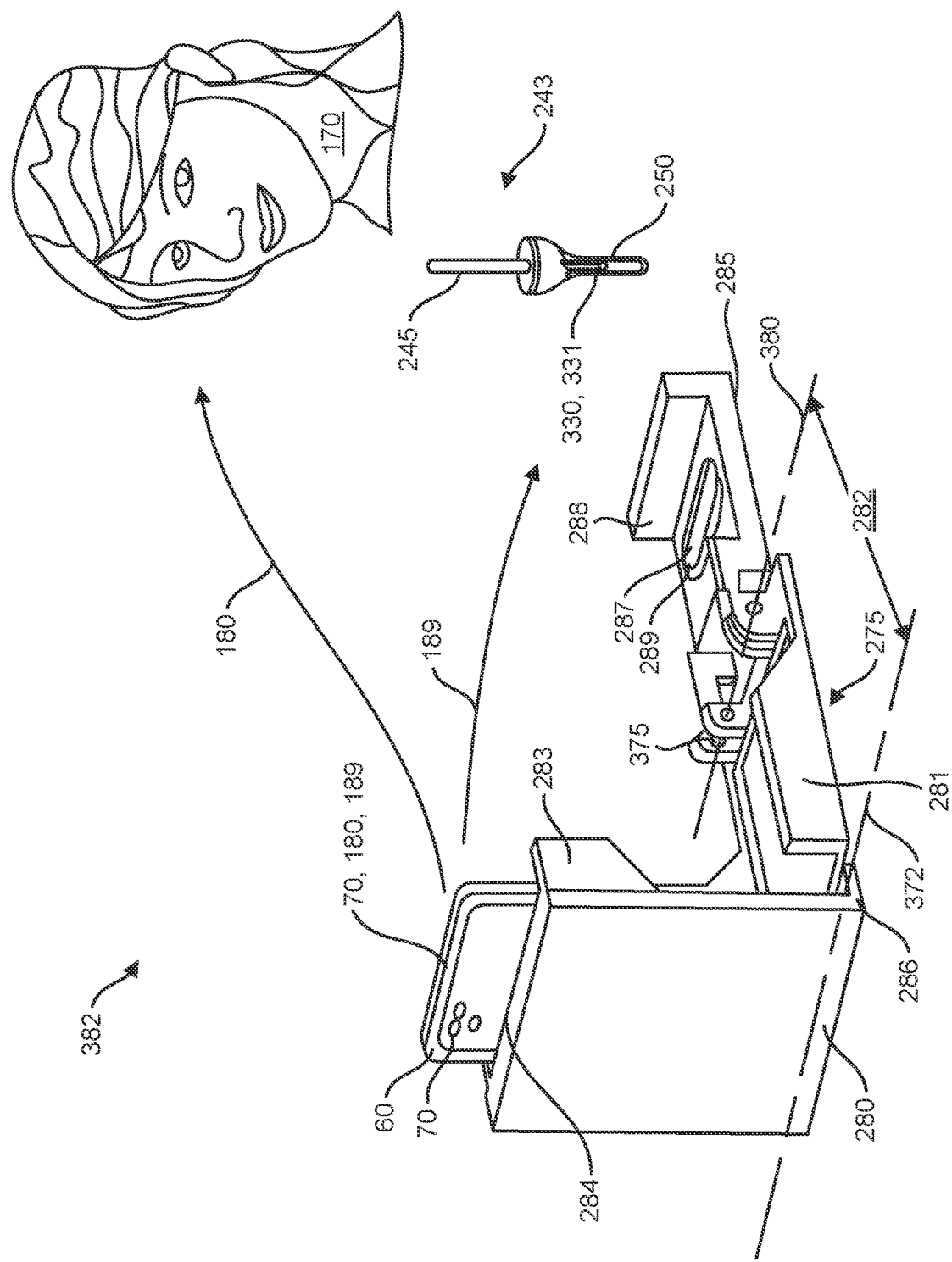
FIG. 12 shows the third step test authentication in the upper perspective view that shows the test stand that is in the second operational state being laid flat, wherein the electronic device is disposed in the left side of the stand with the electronic device including a camera facing to the right that is documenting the nasal swab inserted into the reagent fluid in the extraction buffer tube to mix the nasal secretions with the reagent fluid and with the nasal swab having partial removal from the extraction buffer tube to squeegee the nasal swab secretions into the reagent fluid with the compression step on the extraction buffer tube.
Figure 13:
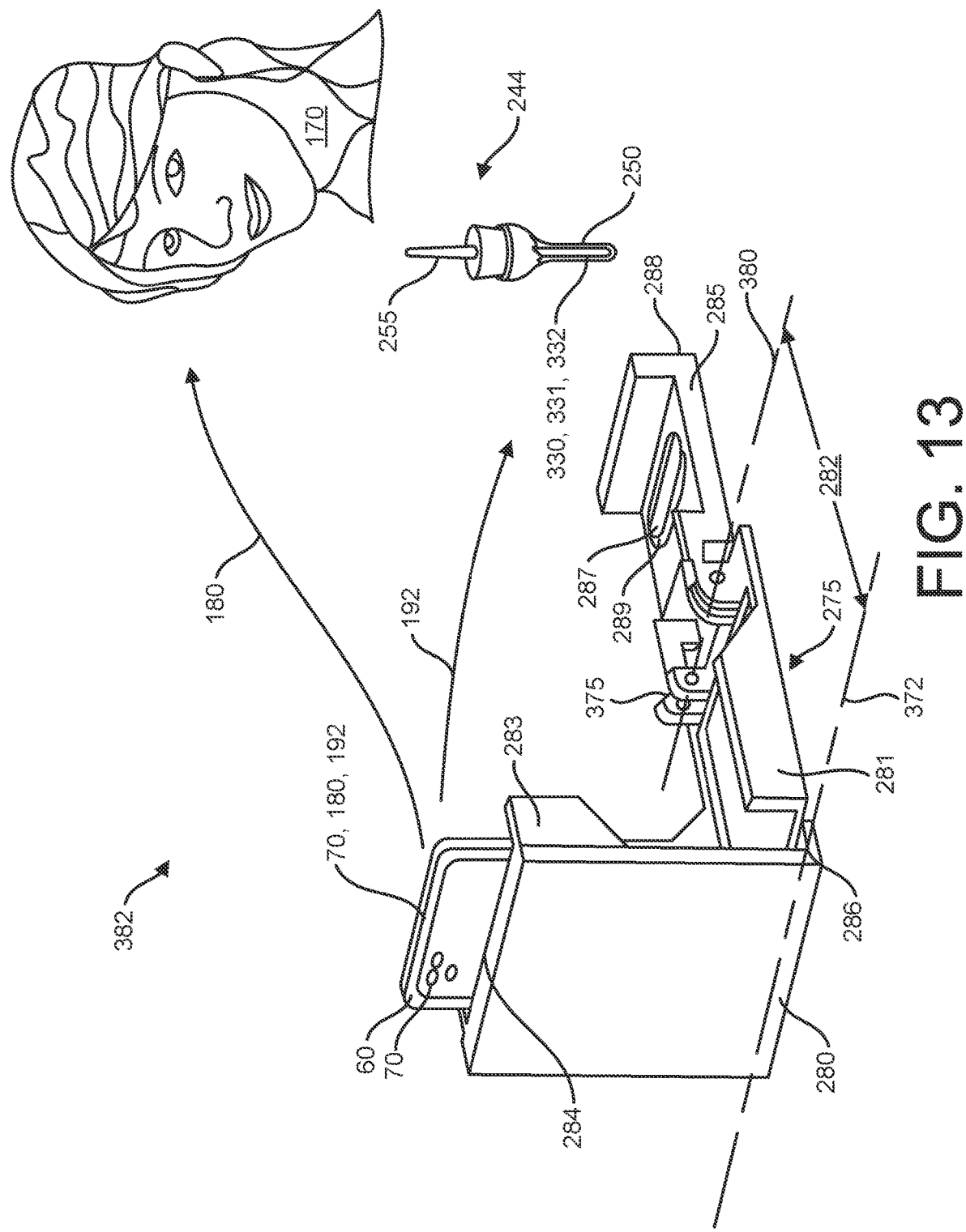
FIG. 13 shows the fourth step test authentication in the upper perspective view that shows the test stand that is in the second operational state being laid flat, wherein the electronic device is disposed in the left side of the stand with the electronic device including a camera facing to the right that is documenting the extraction buffer tube with the nozzle cap in the placing step into the extraction buffer tube with the reagent fluid that contains nasal secretions from the nasal swab.
Figure 14:
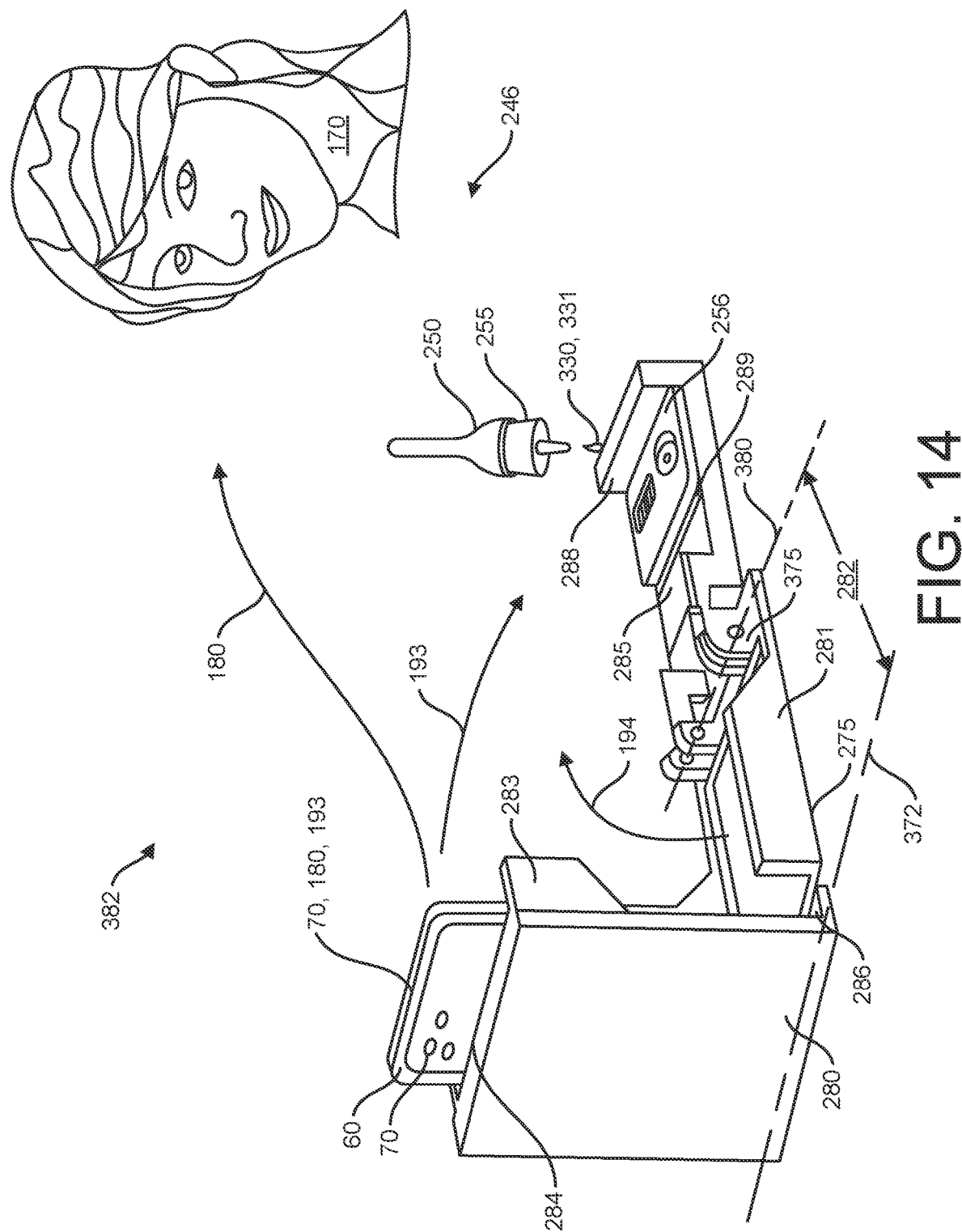
FIG. 14 shows the fifth step test authentication in the upper perspective view that shows the test stand that is in the second operational state being laid flat, wherein the electronic device is disposed in the left side of the stand with the electronic device including a camera facing to the right that is documenting the extraction buffer tube being inverted to release drops from the nozzle cap onto the specimen well of the test card that results in the test card test result window indicating with a test control line and a negative positive test line, wherein the test card is disposed onto the base mount portion of the test stand.
Figure 15:
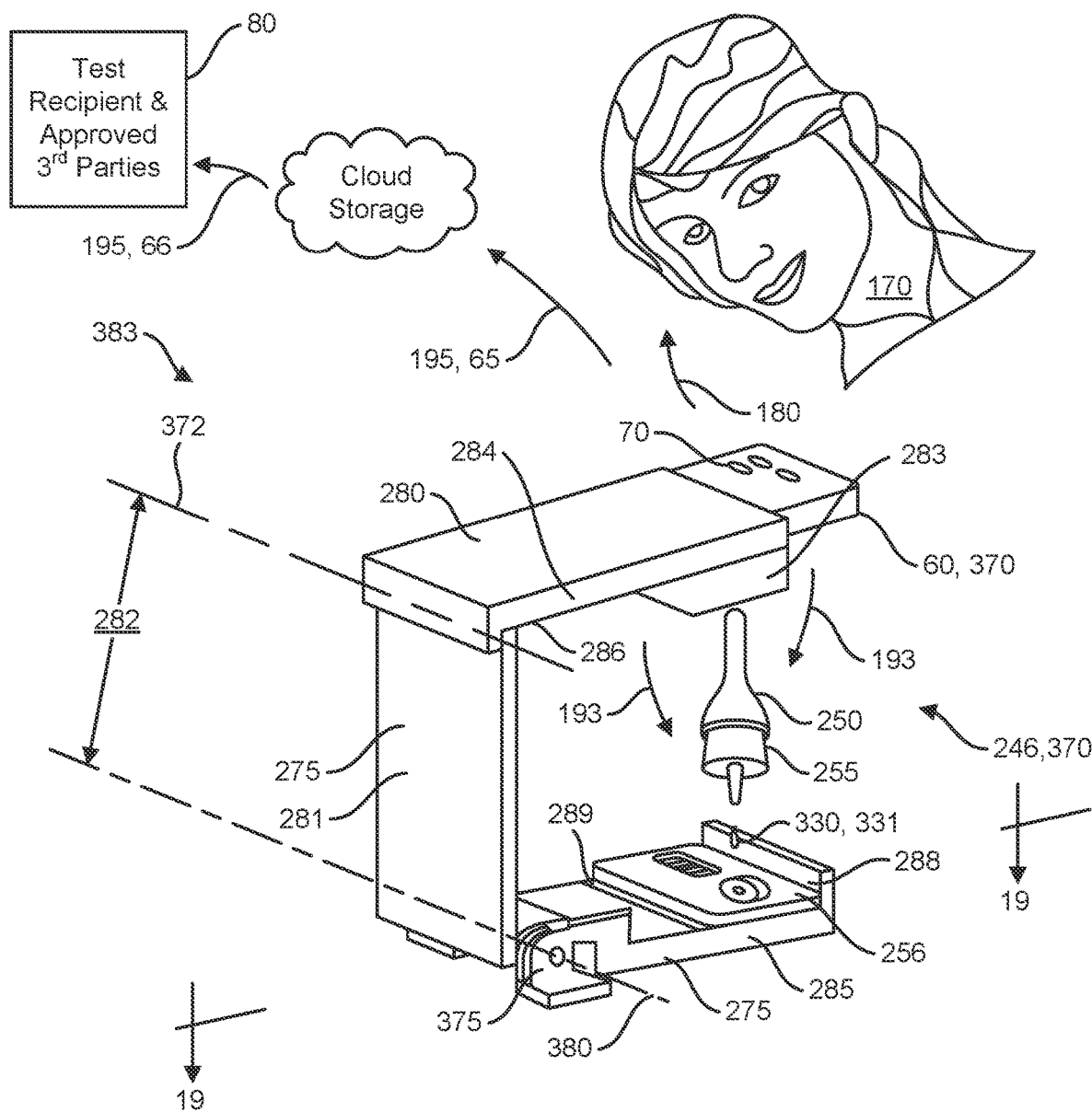
FIG. 15 shows an upper perspective view that shows the test stand that is in the third operational state being partially folded with the electronic device and camera suspended over the base mount portion for taking an authentication video of the test card developing the test result from the extraction buffer tube dripping the reagent fluid and nasal secretion mix onto the test card specimen well.
Figure 16:
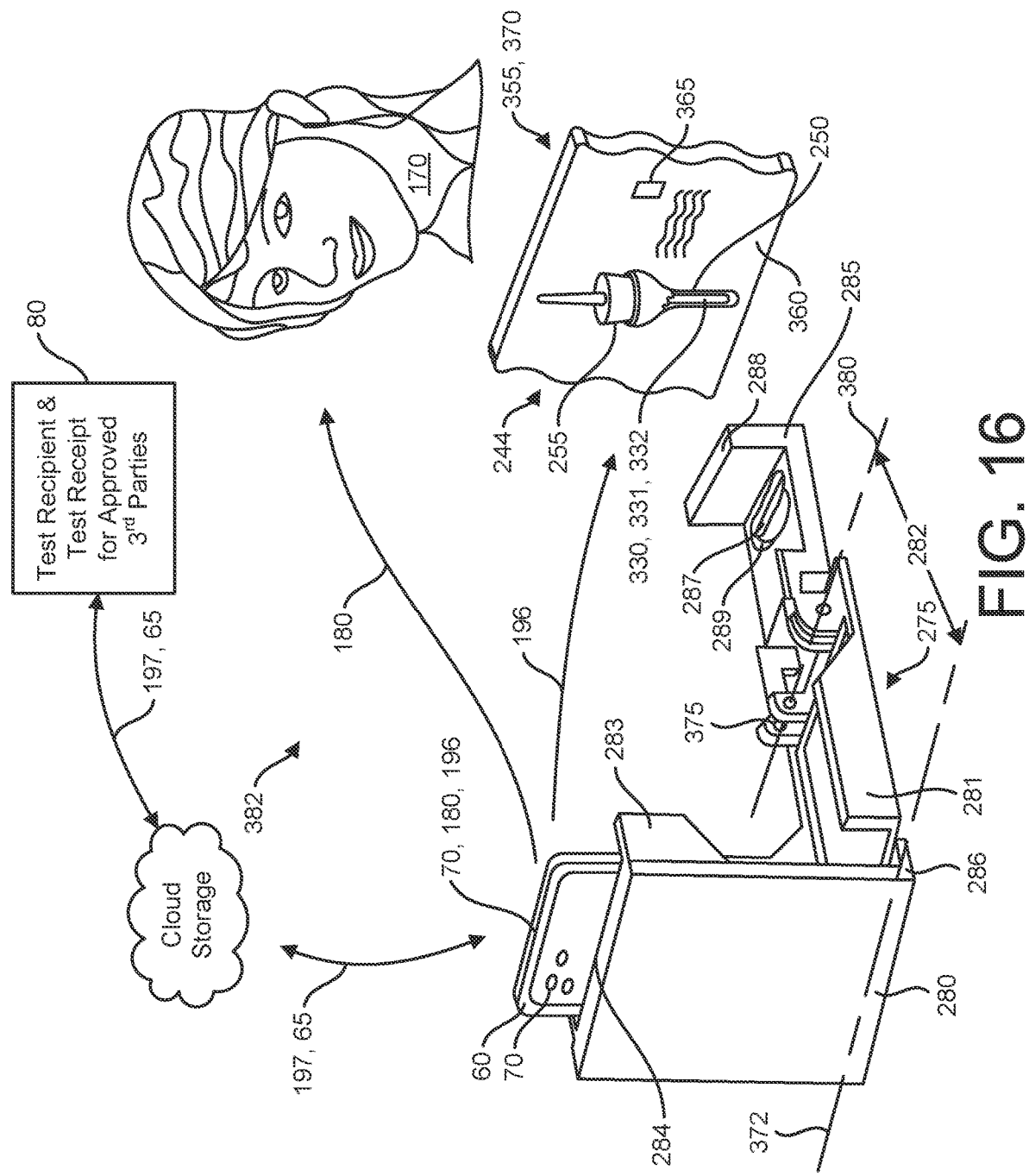
FIG. 16 shows the fourth step test authentication in the upper perspective view that shows the test stand that is in the second operational state being laid flat, wherein the electronic device is disposed in the left side of the stand with the electronic device including a camera facing to the right that is documenting the extraction buffer tube with the nozzle cap in the placing step into the extraction buffer tube with the reagent fluid that contains nasal secretions from the nasal swab being readied for mailing to a remote lab for obtaining a test result.

60 Electronic device
65 Internet connection of the electronic device 60
70 Camera of the electronic device 60
80 Internet portal for review by a third party
85 Nasal secretions
125 Saliva
130 Sputum
165 User interface application on the electronic device 60
170 User of the covid test kit 240
180 Camera of the electronic device 60 or camera 220 verifying a user 170 identity usually via facial recognition
185 Camera of the electronic device 60 verifying COVID test kit 240 components 245, 250, 256 via identification codes 247, 251, 257, 365
186 Camera 70 verifying nasal swab 245 nasal swipe step 241
187 Camera 70 verifying deep sputum 125 extraction step 350 (no induction)
188 Camera 70 verifying nasal swab 245 insertion into extraction buffer tube 250 step 242
189 Camera 70 verifying nasal swab 245 removal from the extraction buffer tube 250 step 243
191 Instructions for use of the COVID test kit 240
192 Camera 70 verifying the sealing of the extraction buffer tube 250 with the nozzle cap 255 step 244
193 Camera 70 verifying the dropping of the nasal secretion fluid mix 330 or saliva fluid mix 331 of the extraction buffer tube 250 and the nozzle cap 255 onto the test card 256 for the test results step 246
194 Pivotal movement of the camera 60 mount portion 280 of the test stand 275 both being in lockstep with one another being about the test stand pivotal attachment 375 and the test stand pivotal axis 380 by about ninety (90) degrees relative to the base 285 of the test stand 275, see FIG. 14 going to FIG. 15 that is to be used after step 246
195 Continuous dynamic communication of the user 170 identity preferably through facial recognition, also the COVID test kit 240 identification codes 247, 251, 257, 365, and test card 256 test results 266, 267 to the internet portal for review by the third party by the electronic device 60 via the internet connection 65
196 Camera 70 verifying the sealing of the extraction buffer tube 250 with the nozzle cap 255 to optionally send the nasal secretion fluid mix 330, saliva fluid mix 331, or sputum fluid mix 332 to an outside lab in a scan verified 365 envelope 360 for step 355
197 Continuous dynamic communication of the user 170 identity preferably through facial recognition, also the COVID test kit 240 identification codes 247, 251, 257, 365, to the internet portal for sending the nasal secretion fluid mix 330 to the outside lab testing for review by the third party by the electronic device 60 via the internet connection 65 with a test result notification back to the electronic device 60
235 COVID antigen testing method
240 Typical COVID antigen test kit
241 First step of nasal swab 245 insertion 310 into the nasal cavity 385, see FIGS. 4 and 10
242 Second step of swab 245 secretion 85, 125 immersion into the extraction buffer tube 250 and reagent fluid 325, see FIGS. 5 and 11
243 Third step of completing the swab 245 secretion 85, 125 removal, see FIGS. 6 and 12
244 Fourth step of removing the swab 245 from the extraction buffer tube 250 and placing 345 the nozzle cap 255 into the extraction buffer tube 250, see FIGS. 7 and 13 or if outside lab see FIG. 16

Figure 9:
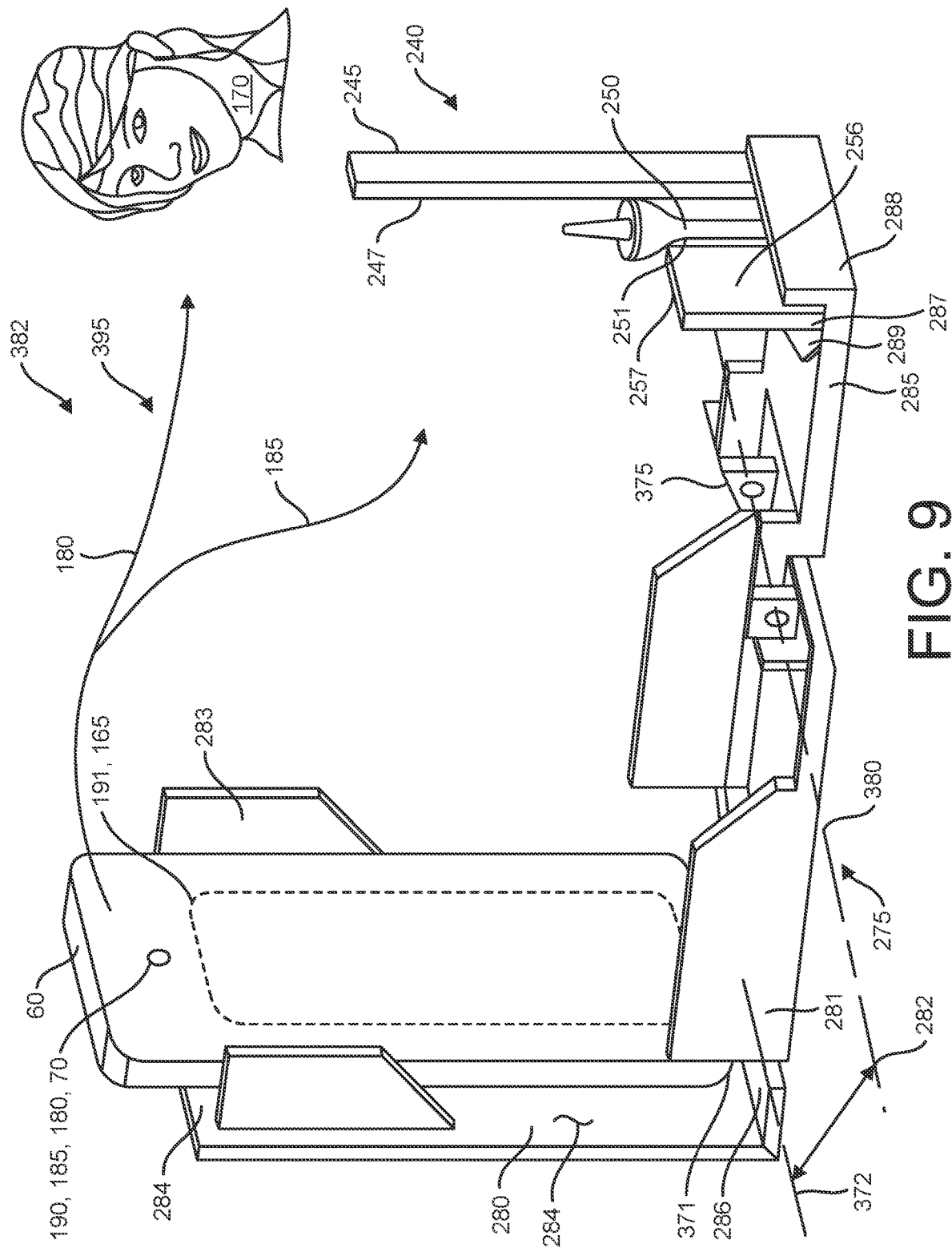
FIG. 9 shows an upper perspective view of the test stand that is in the second operational state being laid flat, wherein an electronic device is disposed in the left side of the stand with the electronic device including a camera facing to the right, further the test kit components are shown disposed in the right side of the test stand that include the nasal swab in the sterile package, the extraction buffer tube with the nozzle cap and the test card that has the test card result window facing the electronic device.
Figure 17:
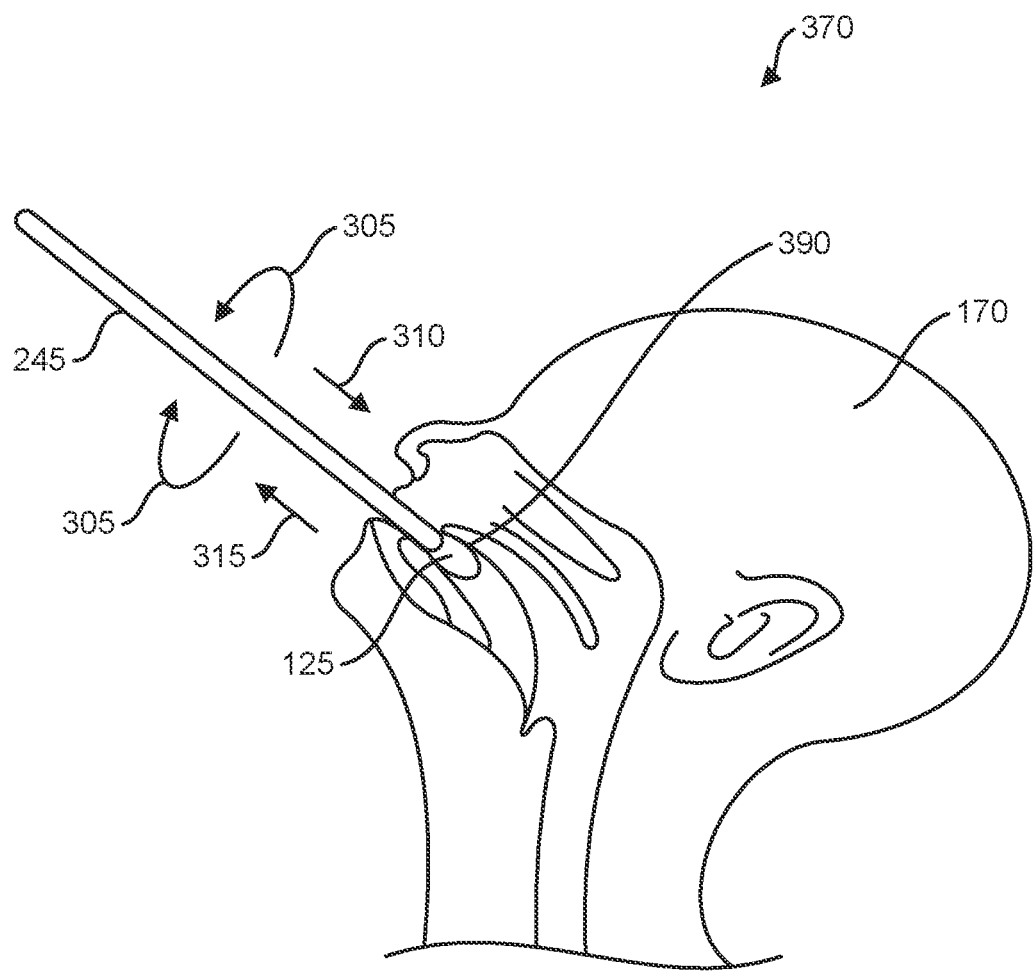
FIG. 17 shows a first step modification that includes a side elevation cross section view of a user with the nasal swab being used orally inserted into their mouth cavity with a rotational and insertion step/removal step movement of the oral swab in relation to the oral cavity to obtain a proper saliva swab sample.
Figure 18:
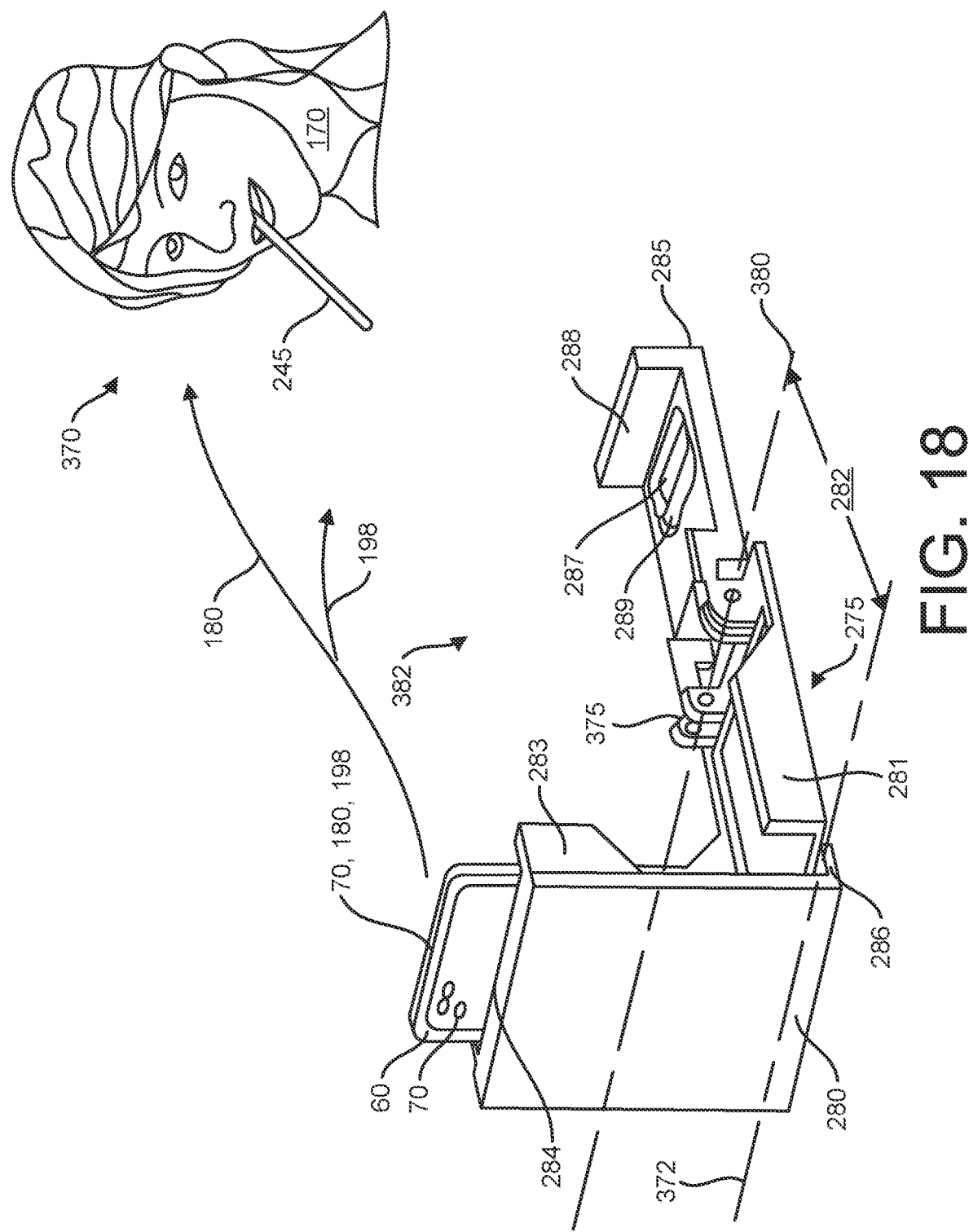
FIG. 18 shows the first step modification test authentication in an upper perspective view that shows the test stand that is in the second operational state being laid flat, wherein the electronic device is disposed in the left side of the stand with the electronic device including a camera facing to the right that is documenting the use of the nasal swab orally by the user.

245 Sterile extended nasal/oral swab in sterile package
246 Fifth step of applying four drops of the nasal secretion fluid mix 330 or the saliva fluid mix 331 to the test card 256 specimen well 260 as received into the test stand 275 shallow cavity 289 of the base mount portion 285 and waiting fifteen minutes—after which control line 266 should appear for valid test and if control line does not appear not test is invalid, if test is valid then if test line 267 appears the test result is positive, if no line appears at 267 then the test result is negative
247 Unique scan code of the swab 245
250 Extraction buffer tube
251 Unique scan code of the extraction buffer tube 250
255 Nozzle cap
256 Test card
257 Unique scan code of the test card 256
260 Specimen well of the test card 256
265 Test result window of the test card 256
266 Test control line for test authenticity of the test card 256
267 Negative/positive test line (line present=positive result/ no line present=negative result) of the test card 256
270 User interface display application on the electronic device 60 for the complete COVID testing method steps 241, 242, 243, 244, 246, 350, 355, 370
275 Test stand or medical testing apparatus
280 Camera 70 mount portion of the test stand 275
281 Camera spacer base portion
282 Selected distance determined by the length of the camera base spacer portion 281 or as between the first pivotal axis 372 and the second pivotal axis 280
283 Compression clamp for the electronic device 60 and camera 70 of the electronic device 60
284 Back support for the electronic device 60 and camera 70 of the electronic device 60
285 Base mount portion of the test stand 275 that is sized and configured to receive the test kit 240 that includes the nasal/oral swab 245 with code 247, the extraction buffer tube 250 with reagent 325 all having code 251, stopper 255, and test card 256 (vertically) with code 257, all in deep cavity 287 for step 395, see FIG. 9, plus the base mount portion 285 alternatively receives the test card 256 (horizontally or lay flat) in shallow cavity 289, for step 246, see FIG. 14
286 Bottom support for the electronic device 60 and camera 70 of the electronic device 60
287 Deep cavity of the base mount portion 285
288 Partial end extension of the base mount portion 285
289 Shallow cavity of the base mount portion 285
300 COVID test nasal swab 245 insert procedure steps, 305, 310, 315 into the nasal cavity 385, see FIG. 4
301 First perimeter of the deep cavity 287
302 Second perimeter of the shallow cavity 289
303 Shared perimeter as between the first 301 and second 302 perimeters
305 Rotation step of the swab 245 both ways four times for fifteen seconds, see FIG. 4
310 Insertion step of the nasal swab 245 parallel to the palate until resistance is met, see FIG. 4
315 Remove step for swab 245 after completing steps 305, 310 and repeat in other nostril 385 using the same nasal swab 245, see FIG. 4
320 Rotate step for the swab 245 at least ten times both ways, see FIG. 5
325 Reagent fluid disposed within the extraction tube 250, see FIG. 5
330 Nasal secretion 85 mixed with the reagent 325
331 Saliva 125 mixed with the reagent 325
332 Sputum 130 mixed with the reagent 325
335 Partial removal of the swab 245 from the extraction buffer tube 250 to accomplish step 243 to squeegee the nasal secretion 85 mixed with the reagent 325 combination 330 from the nasal swab 245, see FIGS. 6 and 12
340 Compressing step of the flexible extraction tube 250 to accomplish step 335, see FIGS. 6 and 12
345 Placing step of the nozzle cap 255 into the extraction buffer tube 250 to accomplish step 244, see FIGS. 7, 13, and 16
350 Modification of step 243 to step 243A of inserting the swab 245 with the saliva 125 or sputum 130 directly into the extraction tube 250 with the reagent 325 to be sent to an outside lab for results, see FIGS. 6, 10, and 16, then moving toward step 244
355 Modification of step 244 to step 244A as shown in FIG. 16 when the specimen 330, 331, 332 is to be sent to an outside lab for results
360 Sealed envelope for sending the sample 330, 331, 332 to the outside lab, see FIG. 16
365 Unique scan code for the envelope 360
370 Modification of step 241 to step 241A for saliva swab 245 that in addition to steps 305, 310, 315, the saliva swab 245 should be moved to rub the inside of the checks, above and below the tongue, rub the gums, and the hard palate all of the oral cavity 390, then moving to step 242, see FIGS. 17 and 18
371 First pivotal attachment of the test stand 275
372 First pivotal axis of the test stand 275
375 Second pivotal attachment of test stand 275
380 Second pivotal axis of the pivotal attachment 375
381 First operational state of the test stand 275 that is closed and folded
382 Second operational state of the test stand 275 that is laid flat
383 Third operational state of the test stand 275 that is partially folded with the electronic device 50 and camera 70 suspended over the base mount portion for taking a video on the test card 256, see FIG. 15
385 Nasal cavity
390 Oral cavity
395 Initial verification of the user 170 and test kit 240 that includes the nasal/oral swab 245 with code 247, extraction buffer tube 250 with reagent 325 all having code 251, stopper 255, and test card 256 with code 257

DETAILED DESCRIPTION

Figure 1:
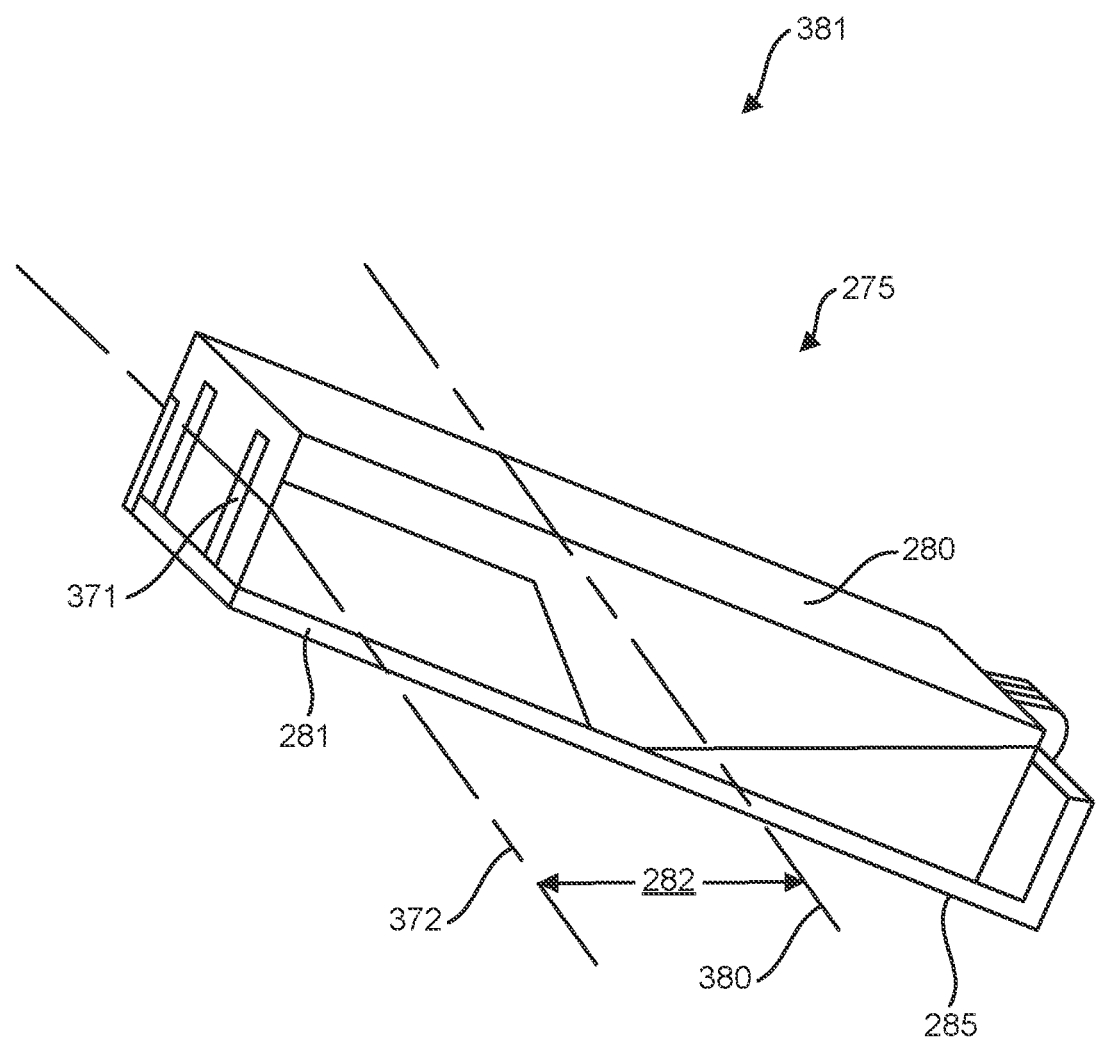
FIG. 1 shows an upper perspective view of the test stand that is in the first operational state being closed and folded with a first pivotal axis and a second pivotal axis that are at a selected distance apart.

With initial reference to FIG. 1 shown is an upper perspective view of the test stand 275 that is in the first operational state 381 being closed and folded with a first pivotal axis 371 and a second pivotal axis 380 that are at a selected distance apart 282.

Figure 2:
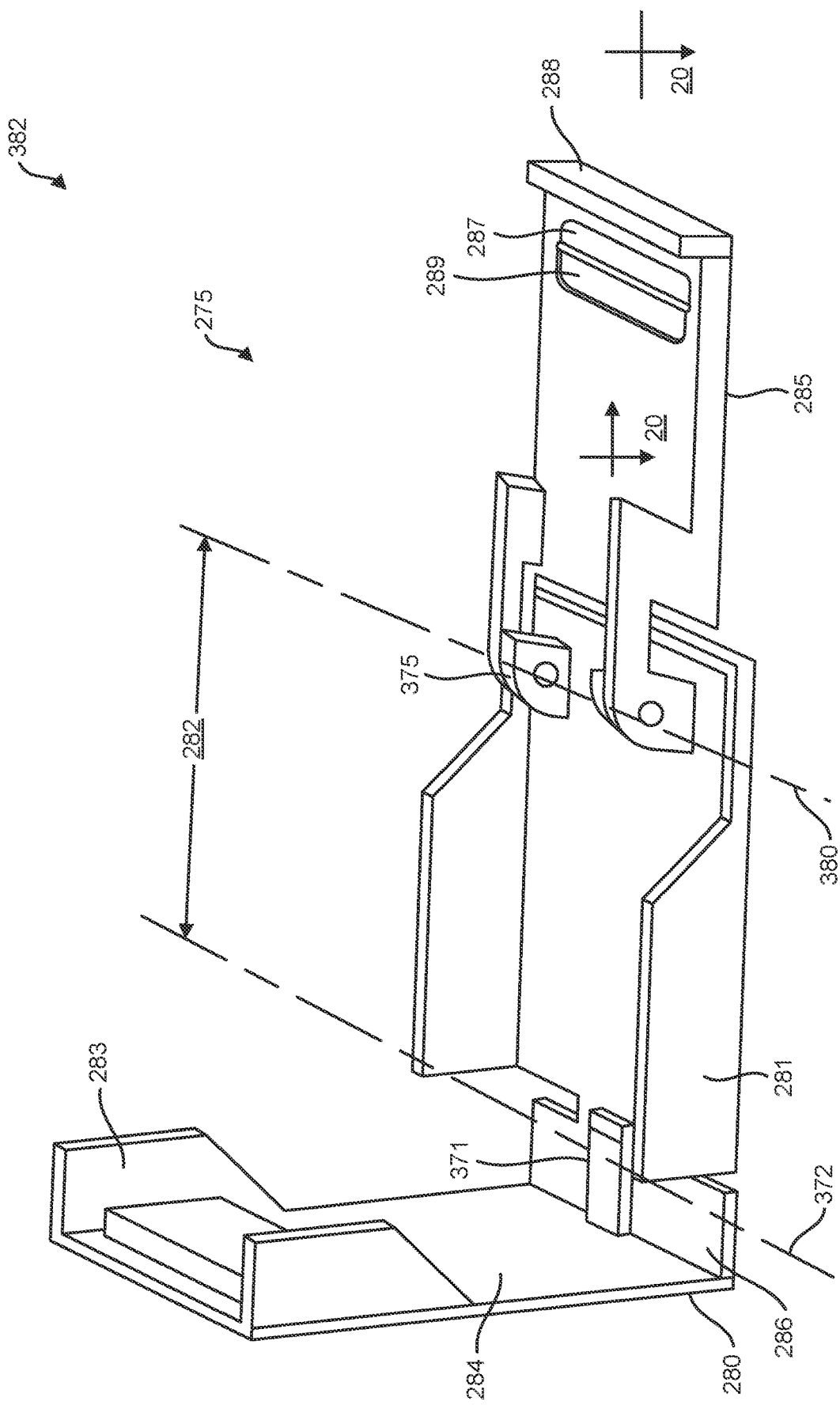
FIG. 2 shows an upper perspective view of the test stand that is in the second operational state being laid flat with the first pivotal axis and the second pivotal axis that are at the selected distance apart, also shown is a deep cavity, a shallow cavity, a base mount portion that terminates in a partial end extension.

Continuing, FIG. 2 shows an upper perspective view of the test stand 275 that is in the second operational state 382 being laid flat with the first pivotal axis 371 and the second pivotal axis 380 that are at the selected distance apart 282, also shown is a deep cavity 287, a shallow cavity 289, a base mount portion 285 that terminates in a partial end extension 288.

Figure 3:
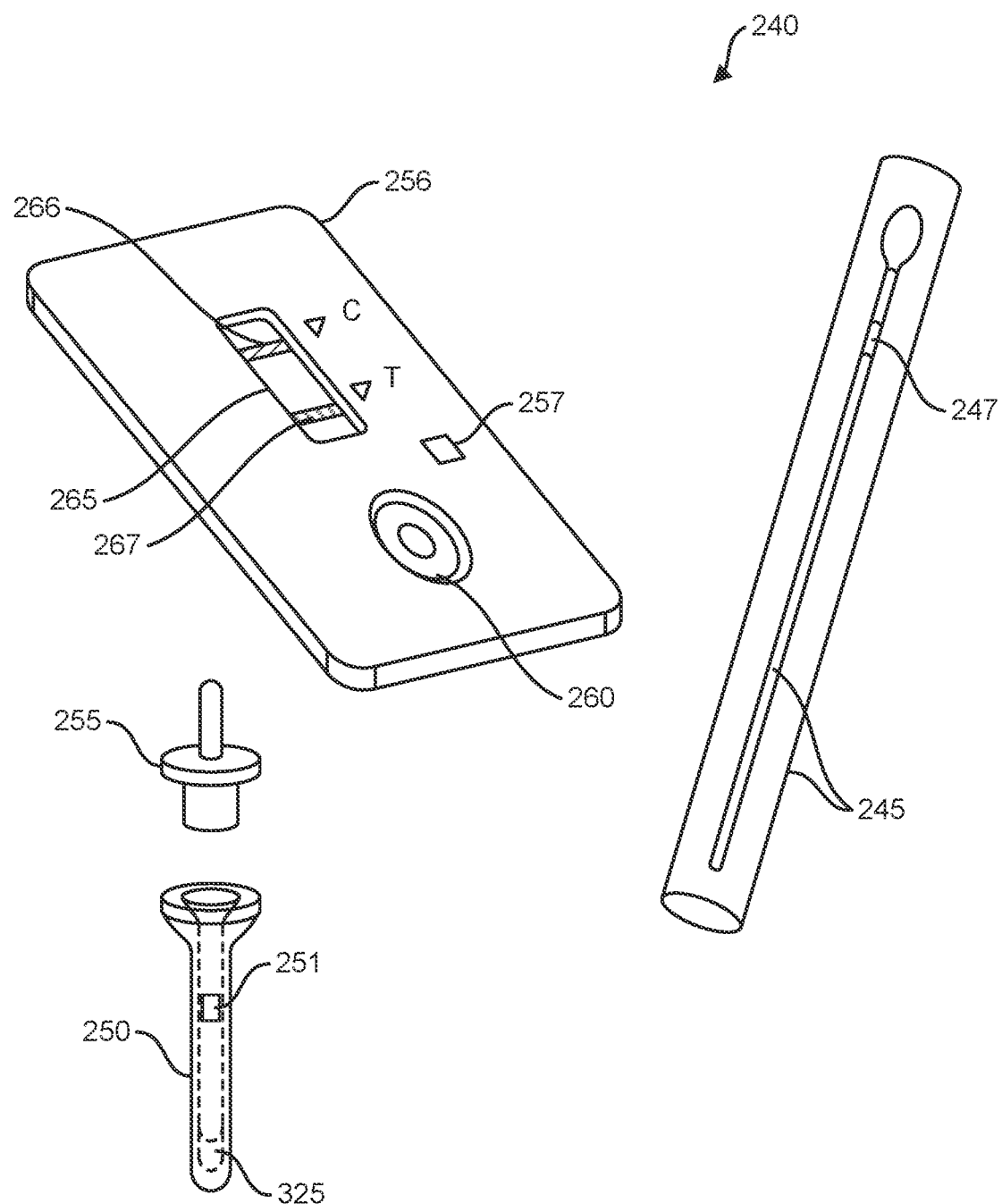
FIG. 3 shows an exploded perspective view of components of a test kit that includes a sterile nasal/oral swab with a unique scan code with the swab in a package, an extraction buffer tube with a unique scan code, a nozzle cap for the extraction buffer tube, a test card that has a specimen well and a test result window.

Next, FIG. 3 shows an exploded perspective view of components of a test kit 240 that includes a sterile nasal/oral swab 245 with a unique scan code 247 with the swab 245 in a package 245, an extraction buffer tube 250 with a unique scan code 251, a nozzle cap 255 for the extraction buffer tube 250, a test card 256 that has a specimen well 260 with a unique scan code 257 and a test result window 265.

Moving onward, FIG. 4 shows a first step 241 that includes a side elevation cross section view of a user 170 with the nasal swab 245 inserted into their nasal cavity 385 with a rotational 305 and insertion step 310/removal step 315 movement of the nasal swab 245 in relation to the nasal cavity 385 to obtain a proper nasal swab 245 nasal secretion 85 sample.

Further, FIG. 5 shows a second step 242 that includes an upper perspective view of the extraction buffer tube 250 with the nasal swab 245 inserted into a reagent fluid 325 commensurating with a rotation step 320 of the nasal swab 245 in the reagent fluid 325.

Continuing, FIG. 6 shows a third step 243 that includes an upper perspective view of the extraction buffer tube 250 with the nasal swab 245 with partial removal 335 from the extraction buffer tube 250 to squeegee the nasal swab 245 from the reagent fluid 325 via a compression step 340 on the extraction buffer tube 250 to place nasal secretions 85 into the reagent fluid 325.

Next, FIG. 7 shows a fourth step 244 that includes an upper perspective view of the extraction buffer tube 250 with the nozzle cap 255 in a placing step 345 into the extraction buffer tube 250 with the reagent fluid 325 that contains nasal secretions 85 from the nasal swab 245.

Figure 8:
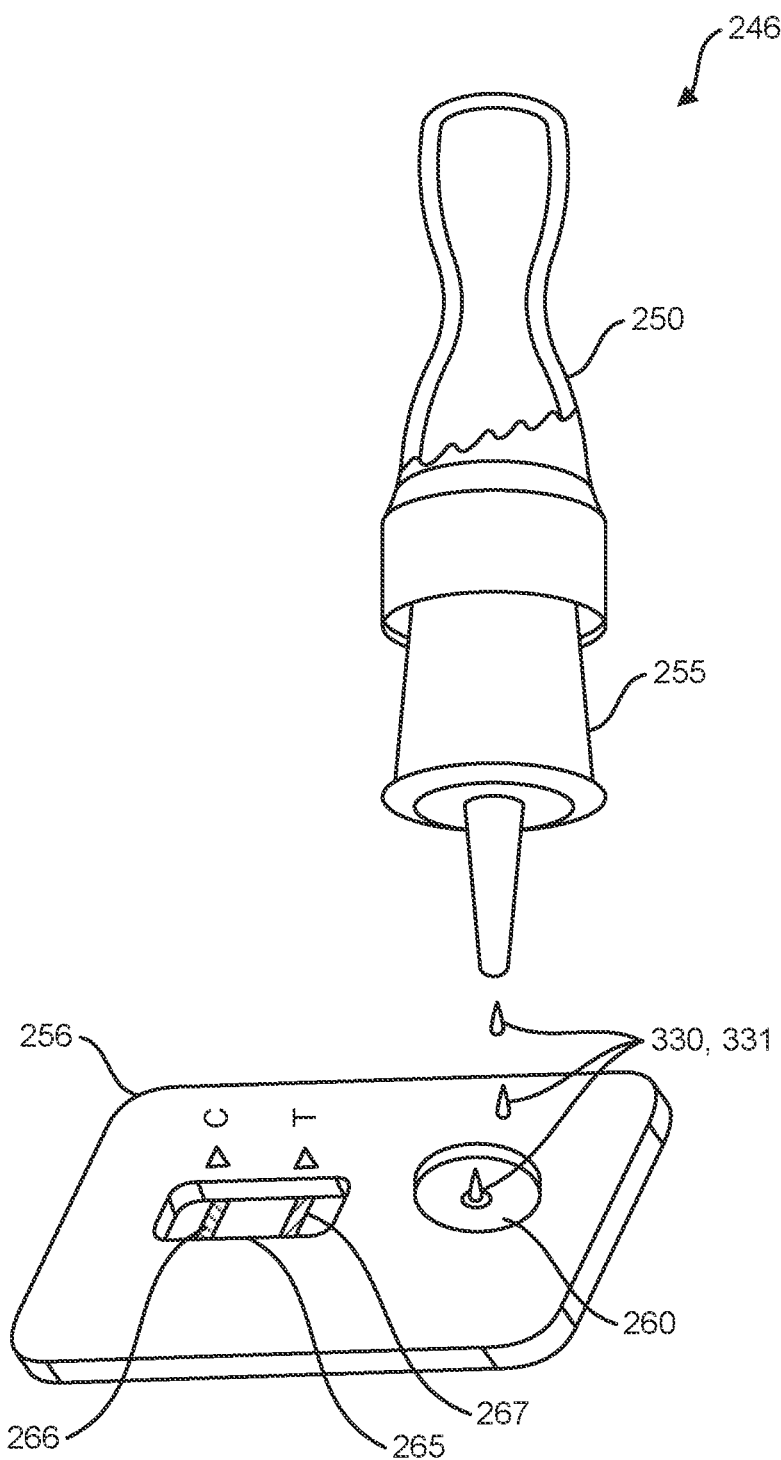
FIG. 8 shows a fifth step that includes an upper perspective view of the extraction buffer tube inverted to release drops from the nozzle cap onto the specimen well of the test card that results in the test card test result window indicating with a test control line and a negative positive test line.

Further, FIG. 8 shows a fifth step 246 that includes an upper perspective view of the extraction buffer tube 250 inverted to release drops 330, 331 from the nozzle cap 255 onto the specimen well 260 of the test card 256 that results in the test card 256 test result window 265 indicating with a test control line 266 and a negative/positive test line 267.

Moving ahead, FIG. 9 shows an upper perspective view of the test stand 275 that is in the second operational state 382 being laid flat, wherein an electronic device 60 is disposed in the left side of the stand 275 with the electronic device 60 including a camera 70 facing to the right, further the test kit 240 components are shown disposed in the right side of the test stand that include the nasal swab 245 in the sterile package, the extraction buffer tube 250 with the nozzle cap 255 and the test card 256 that has the test card result window 265 facing the electronic device 60.

Next, FIG. 10 shows the first step 241 test authentication in an upper perspective view that shows the test stand 275 that is in the second operational state 382 being laid flat, wherein the electronic device 60 is disposed in the left side of the stand with the electronic device 60 including the camera 70 facing to the right that is documenting the use of the nasal swab 245 by the user 170, plus shown is the extraction buffer tube 250 with saliva 125 and sputum 130.

Continuing, FIG. 11 shows the second step 242 test authentication in the upper perspective view that shows the test stand 275 that is in the second operational state 382 being laid flat, wherein the electronic device 60 is disposed in the left side of the stand 275 with the electronic device 60 including the camera 70 facing to the right that is documenting the nasal swab 245 inserted into the reagent fluid 325 in the extraction buffer tube 250.

Moving onward, FIG. 12 shows the third step 243 test authentication in the upper perspective view that shows the test stand 275 that is in the second operational state 382 being laid flat, wherein the electronic device 60 is disposed in the left side of the stand with the electronic device 60 including the camera 70 facing to the right that is documenting the nasal swab 245 inserted into the reagent fluid 325 in the extraction buffer tube 250 to mix the nasal secretions 85 with the reagent fluid 325 and with the nasal swab 245 having partial removal 335 from the extraction buffer tube 250 to squeegee the nasal swab 245 secretions 85 into the reagent fluid 325 with the compression step 340 on the extraction buffer tube 250.

Next, FIG. 13 shows the fourth step 244 test authentication in the upper perspective view that shows the test stand 275 that is in the second operational state 382 being laid flat, wherein the electronic device 60 is disposed in the left side of the stand 275 with the electronic device 60 including the camera 70 facing to the right that is documenting the extraction buffer tube 250 with the nozzle cap 255 in the placing step 345 into the extraction buffer tube 250 with the reagent fluid 325 that contains nasal secretions 85 from the nasal swab 245.

Further, FIG. 14 shows the fifth step 246 test authentication in the upper perspective view that shows the test stand 275 that is in the second operational state 382 being laid flat, wherein the electronic device 60 is disposed in the left side of the stand 275 with the electronic device 60 including the camera 70 facing to the right that is documenting the extraction buffer tube 250 being inverted to release drops 330, 331 from the nozzle cap 255 onto the specimen well 260 of the test card 256 that results in the test card 256 test result window 265 indicating with the test control line 266 and a negative/positive test line 267, wherein the test card 256 is disposed onto the base mount portion 285 of the test stand 275.

Moving ahead, FIG. 15 shows an upper perspective view that shows the test stand 275 that is in the third operational state 383 being partially folded with the electronic device 60 and camera 70 suspended over the base mount portion 285 for taking an authentication video of the test card 256 developing the test result from the extraction buffer tube 250 dripping the reagent fluid 325 and nasal secretion 85 mix 330, 331 onto the test card 256 specimen well 260.

Continuing, FIG. 16 shows the fourth step 244 test authentication in the upper perspective view that shows the test stand 275 that is in the second operational state 382 being laid flat, wherein the electronic device 60 is disposed in the left side of the stand 275 with the electronic device 60 including the camera 70 facing to the right that is documenting the extraction buffer tube 250 with the nozzle cap 255 in the placing step 345 into the extraction buffer tube 250 with the reagent fluid 325 that contains nasal secretions 85 from the nasal swab 245 being readied for mailing 355 to a remote lab for obtaining a test result.

Further, FIG. 17 shows a first step 241 modification 370 that includes a side elevation cross section view of a user 170 with the nasal swab 245 being used orally inserted into their mouth cavity 390 with a rotational 305 and insertion step 310/removal step 315 movement of the oral swab 245 in relation to the oral cavity 390 to obtain a proper saliva 125 swab sample.

Next, FIG. 18 shows the first step 241 modification 370 test authentication in an upper perspective view that shows the test stand 275 that is in the second operational state 382 being laid flat, wherein the electronic device 60 is disposed in the left side of the stand 275 with the electronic device 60 including the camera 70 facing to the right that is documenting the use of the nasal swab 245 orally by the user 170.

Figure 19:
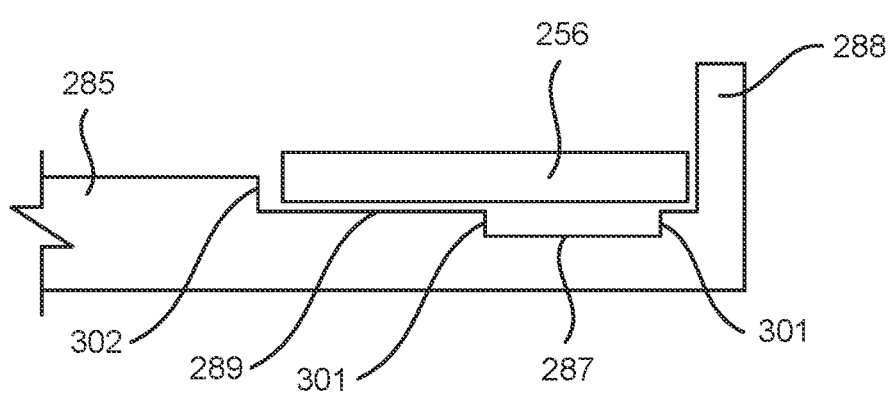

Moving onward, FIG. 19 shows cross section 19-19 from FIG. 15, wherein FIG. 19 shows the test card 256 disposed within the shallow cavity 289 that is in the base mount portion 285 and utilizing the partial end extension 288, with all operational to position and support the test card 256 for authentication via the camera 70 as shown in FIG. 15, note that the deep cavity 287 is also shown in relation to the shallow cavity 289 with the first 301 and second 302 perimeters.

Figure 20:
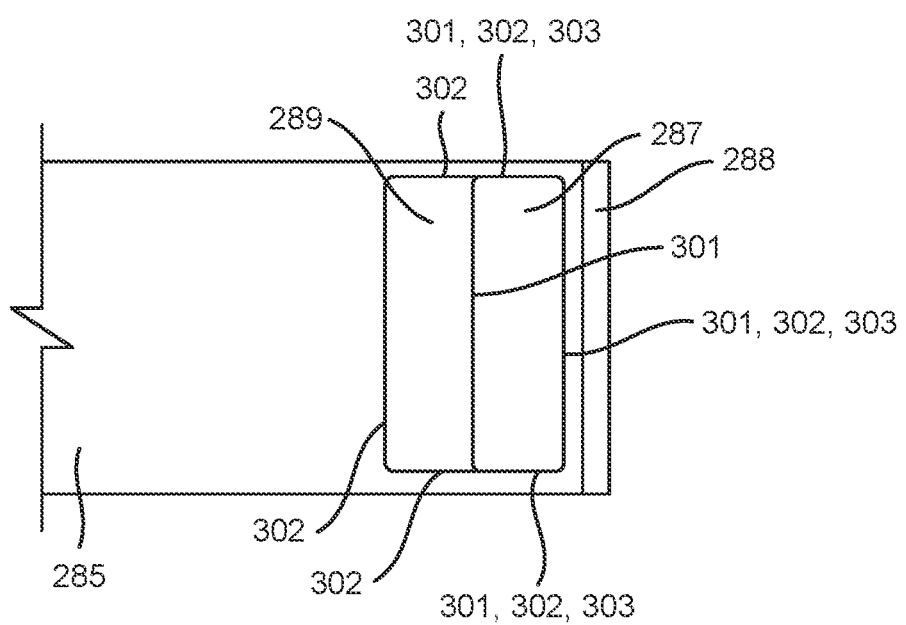

Also, FIG. 20 shows view 20-20 from FIG. 2, wherein FIG. 20 shows the partial end extension 288 along with the base mount portion 285 and the deep cavity 287 in relation to the shallow cavity 289 with the first 301 and second 302 perimeters along with the shared perimeter 303 that forms a part of the first 301 and second 302 perimeters.

Broadly in referring to FIGS. 1-20, the present invention is a medical testing apparatus 275 for the user 170 to help to authenticate and track the process/method of use 235 of the separate test kit 240 that is received partially into the medical test apparatus 275, wherein the test kit 240 that includes components of the extended nasal/oral swab 245, the buffer tube 250, the reagent fluid 325 disposed within the buffer tube 250, the nozzle cap 255, and the test card 256. The test kit 240 is for testing to obtain a test result of a presence or a non-presence of an infection that utilizes the internet connected electronic device 60 with the camera 70 for communication 65, 195 of the authentication and tracking process to third parties, see in particular FIG. 15.

The medical testing apparatus 275 includes the test stand 275 that is sized and configured to partially receive the electronic device 60 and to partially receive the test kit 240 in a positional alignment to operationally facilitate the camera 70 to more accurately record 185 an unique identification code 247, 251, 257, 365 for each test kit 240 component, and for the camera 70 to identify user 170 facial recognition 180, further the test stand 275 records the test kit 240 process steps using the camera 70 including the presence or non-presence of the infection via the test card 256 test result window 265, see FIGS. 8, 14, and 15.

As an option for the medical testing apparatus 275, wherein the test stand 275 can further comprise the base mount portion 285 that has the first pivotal attachment 371 to a camera mount portion 280, wherein the test stand first pivotal attachment 371 is about the first pivotal axis 372, wherein operationally the test stand 275 camera mount portion 280 in the test stand 275 second operational state 382 facilitates the electronic device 60 and its camera 70 to vertically face the user 170 as the camera mount portion 280 is substantially perpendicular to the base mount portion 285, as best shown in FIGS. 2, 9, 10, 11, 12, 13, 14, 16, and 18.

As a further option for the medical testing apparatus 275, wherein the test stand 275 can further comprise a spacer base portion 281 that is disposed between the camera mount portion 280 and the base mount portion 285 wherein a second pivotal attachment 375 about the second pivotal axis 380 is disposed between the base mount portion 285 and the spacer base portion 281, wherein operationally the second pivotal attachment 375 operationally facilitates the electronic device 60 and its camera 70 to pivot to face toward the base mount portion 285 at a selected distance 282 that is between the first 372 and second 380 axes to enable the camera 70 to operationally video document 193 the test card 256 test results 265, see in particular FIG. 15, plus FIGS. 2, 9, 10, 11, 12, 13, 14, 16, and 18.

As another option for the medical testing apparatus 275, wherein the test stand 275 camera mount portion 280 can further comprise a compression clamp 283, a back support portion 284, and a bottom support portion 286, wherein the compression clamp 283, the back support portion 286, and the bottom support portion 286 are operational to position and support the electronic device 60 camera 70 for the authentication, tracking the test process 180, 185, 186, 187, 188, 189, 192, 193, 194, 195, 196, and 197, and the test result correctly. Further, the compression clamp 283, the back support portion 284, and the bottom support portion 286 provide a support for suspending the electronic device 60 camera 70 over the base mount portion 285 to video the test result from the test card 256, see in particular FIG. 15, plus FIGS. 2, 9, 10, 11, 12, 13, 14, 16, and 18.

Alternatively, for the medical testing apparatus 275, wherein the test stand 275 base mount portion 285 can further comprise the deep cavity 287 having the first perimeter 301 with the partial end extension 288 to partially receive the test kit 240 including for the separable components being the extended nasal/oral swab 245, the buffer tube 250, and the test card 256 for the operational purpose of positionally locating the unique identification codes 247, 251, 257, 365 on the test kit 240 components of the extended nasal/oral swab 245, the buffer tube 250, and the test card 256 for the camera 70 to record 185, see in particular FIGS. 19 and 20, plus FIGS. 2, 9, 10, 11, 12, 13, 14, 15, 16, and 18.

A further alternative for the medical testing apparatus 275, wherein the test stand 275 base mount portion 285 can further comprise a shallow cavity 289 having the second perimeter 302 with the partial end extension 288 to partially receive the test kit card 256, see FIG. 19, for the operational purpose of positionally locating the unique identification code 257 on the test card 256 and test result 265 on the test card 256 for the camera 70 to record, wherein the shallow cavity 289 is shallow in relation to the deep cavity 287 and the second perimeter 302 is greater than the first perimeter 301, further wherein the first 301 and second 302 perimeters partially both have the shared perimeter 303 adjacent to the partial end extension 288, see in particular FIGS. 19 and 20, plus FIGS. 2, 9, 10, 11, 12, 13, 14, 15, 16, and 18.

A continuing alternative for the medical testing apparatus 275, can further comprise a user interface application 165 on the electronic device 60 that is received into the test stand 275, wherein the user interface application 165 which can include instructions 191 for use of the test kit 240 see FIG. 9, the user interface application 165 operationally facilitates the camera 70 video dynamic and continuous documenting of the user 170 including the user's identification 180, tracking the test kit 240 process steps 395 that include placing the test kit 240 into the base mount portion 285 of the test stand 275 for the electronic device 60 camera 70 to scan the identification codes 247, 251, 257, 365 for each of the test kit 240 components that include the extended nasal/oral swab 245, the buffer tube 250 with reagent 325 disposed within the buffer tube 250, the nozzle cap 255, and the test card 256, see FIG. 9, while simultaneously verifying 180 the user 170 identity, again see FIG. 9.

Next verifying the test kit 240 process starting with the step 241 of insertion 310 of the nasal or oral swab 245 by the user 170 to obtain a nasal secretion 85 or saliva 125 on the swab 245, see FIG. 4. A next step 242 of inserting of the nasal or oral swab 245 into the extraction buffer tube 250 with the swab 245 disposed in the reagent fluid 325 with rotating agitation 320 of the nasal or oral/swab 245 in the reagent fluid 325, see FIG. 5, a further step 243 of removing 335 the nasal/oral swab 245 from the extraction buffer tube 250 while compressing 340 the extraction buffer tube 250 to squeegee the nasal/oral swab 245 into the extraction buffer tube 250 thus creating a nasal section fluid mix 330 or a saliva fluid mix 331, see FIG. 6, further sputum 130 could be mixed 332 with the reagent fluid 325 with step 243, 350, see FIGS. 10 and 12, without the use of the nasal/oral swab 245. A continuing step of placing 345 the nozzle cap 255 onto the extraction buffer tube 250, see FIG. 7.

A next step 246 of placing the test card 256 flat to be specifically positionally received into the base mount portion 285 of the test stand 275 then applying drops 330, 331 of the nasal section fluid mix or saliva fluid mix into the specimen well 260 of the test card 256, see FIGS. 8, 14, and 15. Then initiating pivotal movement 194 in going from FIG. 14 to FIG. 15, of the camera mount portion 280 of the test stand 275 of about ninety degrees to align the camera 70 to verify the test results of the presence or non-presence of an infection as indicated by the test card 256 test result window 265 control line 266 and negative/positive test lines 267 after a selected period of time, wherein the test results, user 170 authentication 180, and verification of the test process steps are further communicated 65, 195 to an internet portal for a third party to have access to the test result, user 170 authentication 180, and verification of the test process steps 270, 300, again see FIGS. 14 and 15.

A medical testing apparatus 275 for helping to authenticate and track the process of collecting test samples from a separate test kit 240 that is received partially into the medical test apparatus 275, wherein the test kit 240 includes components of the extended nasal/oral swab 245, the buffer tube 250, the reagent fluid 325 disposed within the buffer tube 250, and the nozzle cap 255. The medical testing apparatus 275 documenting the transfer of the test sample 330, 331, 332 to a remote laboratory that will determine the presence or non-presence of an infection, see in particular FIG. 16. Wherein the medical testing apparatus 275 utilizes an internet connected 65 electronic device 60 with the camera 70 for communication 65 of the authentication and tracking process 180, 185, 186, 187, 188, 189, 192, 193, 196, and 197 to the remote laboratory in step 244, 355 in a sealed envelope 360 that has unique scan code 365, wherein the internet connected 65 device 60 conveys the presence or non-presence of the infection from the remote laboratory to the medical testing apparatus 275 via the electronic device 60 through the internet 65.

The medical testing apparatus 275 includes the test stand 275 that is sized and configured to partially receive the electronic device 60 and to partially receive the test kit 240 in a positional alignment to operationally facilitate the camera 70 to more accurately record 185 an unique identification code 247, 251, 257, 365 for each test kit 240 component, and for the camera 70 to identify user 170 facial recognition 180, further the test stand 275 records the test kit 240 process steps using the camera 70 including the presence or non-presence of the infection via the test card 256 test result window 265, see FIGS. 8, 14, 15, and 16.

As an option for the medical testing apparatus 275, wherein the test stand 275 can further comprises the base mount portion 285 that has the first pivotal attachment 371 to a camera mount portion 280, wherein the test stand first pivotal attachment 371 is about the first pivotal axis 372, wherein operationally the test stand 275 camera mount portion 280 in the test stand 275 second operational state 382 facilitates the electronic device 60 and its camera 70 to vertically face the user 170 as the camera mount portion 280 is substantially perpendicular to the base mount portion 285, as best shown in FIGS. 2, 9, 10, 11, 12, 13, 14, 16, and 18.

As a further option for the medical testing apparatus 275, wherein the test stand 275 can further comprise a spacer base portion 281 that is disposed between the camera mount portion 280 and the base mount portion 285 wherein a second pivotal attachment 375 about the second pivotal axis 380 is disposed between the base mount portion 285 and the spacer base portion 281, wherein operationally the second pivotal attachment 375 operationally facilitates the electronic device 60 and its camera 70 to pivot to face toward the base mount portion 285 at a selected distance 282 that is between the first 372 and second 380 axes to enable the camera 70 to operationally video document 193 the test card 256 test results 265, see in particular FIG. 15, plus FIGS. 2, 9, 10, 11, 12, 13, 14, 16, and 18.

As another option for the medical testing apparatus 275, wherein the test stand 275 camera mount portion 280 further comprises a compression clamp 283, a back support portion 284, and a bottom support portion 286, wherein the compression clamp 283, the back support portion 286, and the bottom support portion 286 are operational to position and support the electronic device 60 camera 70 for the authentication, tracking the test process 180, 185, 186, 187, 188, 189, 192, 193, 194, 195, 196, and 197, and the test result correctly, further to provide a support for suspending the electronic device 60 camera 70 over the base mount portion 285 to video the test result from the test card 256, see in particular FIG. 15, plus FIGS. 2, 9, 10, 11, 12, 13, 14, 16, and 18.

Alternatively, for the medical testing apparatus 275, wherein the test stand 275 base mount portion 285 can further comprise the deep cavity 287 having the first perimeter 301 with the partial end extension 288 to partially receive the test kit 240 including for the separable components being the extended nasal/oral swab 245, and the buffer tube 250, for the operational purpose of positionally locating the unique identification codes 247, 251, 365 on the test kit 240 components of the extended nasal/oral swab 245, and the buffer tube 250 for the camera 70 to record 185, see in particular FIG. 16, plus FIGS. 2, 9, 10, 11, 12, 13, 14, 15, 18, 19, and 20.

A continuing alternative for the medical testing apparatus 275, it can further comprise a user interface application 165 on the electronic device 60 that is received into the test stand 275, the user interface application 165 which can include instructions 191 for use of the test kit 240 see FIG. 9, wherein the user interface application 165 operationally facilitates the camera 70 video dynamic and continuous documenting of the user 170 including the user's identification 180, tracking the test kit 240 process steps 395 that include placing the test kit 240 into the base mount portion 285 of the test stand 275 for the electronic device 60 camera 70 to scan the identification codes 247, 251, 365 for each of the test kit 240 components that include the extended nasal/oral swab 245, the buffer tube 250 with reagent 325 disposed within the buffer tube 250, and the nozzle cap 255, again see FIG. 9, while simultaneously verifying 180 the user 170 identity, again see FIG. 9.

Next verifying the test kit 240 process starting with the step 241 of insertion 310 of the nasal or oral swab 245 by the user 170 to obtain a nasal secretion 85 or saliva 125 on the swab 245, see FIG. 4. A next step 242 of inserting of the nasal or oral swab 245 into the extraction buffer tube 250 with the swab 245 disposed in the reagent fluid 325 with rotating agitation 320 of the nasal or oral/swab 245 in the reagent fluid 325, see FIG. 5, a further step 243 of removing 335 the nasal/oral swab 245 from the extraction buffer tube 250 while compressing 340 the extraction buffer tube 250 to squeegee the nasal/oral swab 245 into the extraction buffer tube 250 thus creating a nasal section fluid mix 330 or a saliva fluid mix 331, see FIG. 6. A continuing step of placing 345 the nozzle cap 255 onto the extraction buffer tube 250, see FIG. 7.

A next step 244, 355 of placing the extraction buffer tube 250 with the nozzle cap 255 containing the nasal section fluid mix 330 or a saliva fluid mix 331 into the envelope 360 with unique scan code 365 that is all video documented 180, 196 with the user 170 facial recognition as shown in FIG. 16. Verification of the test process steps 244, 355 are further communicated 65, 196 to an internet portal for a third party 80 to have access to the test result, user 170 authentication 180, and verification of the test process steps 270, 300, see FIGS. 9, 10, 11, 12, 13, and 16.

Note that the test kit 240 may or may not be included with the medical testing apparatus 275, as the medical testing apparatus in its base form is the test stand 275.

In the summary above and in this detailed description, and the claims below, and in the accompanying drawings, reference may be made to particular features of the invention. It may be to be understood that the disclosure of the invention in this specification includes all possible combinations of such particular features. For example, where a particular feature may be disclosed in the context of a particular aspect or embodiment of the invention, or a particular claim, that feature can also be used, to the extent possible, in combination with and/or in the context of other particular aspects and embodiments of the invention, and in the invention generally.

Where reference may be made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

"Exemplary" may be used herein to mean "serving as an example, instance, or illustration." Any aspect described in this document as "exemplary" may not be necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item, so a "set of items" may indicate the presence of only one item, or may indicate more items. Thus, the term "set" may be equivalent to "one or more" as used herein.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but may be not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description may be regarded as illustrative instead of restrictive of the present invention.

CONCLUSION

Accordingly, the present invention of a medical test apparatus and method has been described with some degree of particularity directed to the embodiments of the present invention. It should be appreciated, though; that the present invention is defined by the following claims construed in light of the prior art so modifications or changes may be made to the exemplary embodiments of the present invention without departing from the inventive concepts contained therein.

The invention claimed is:

1. A medical testing apparatus for a user to help to authenticate and track the process of a separate test kit that is received partially into said medical test apparatus wherein the test kit that includes components of an extended nasal/oral swab, a buffer tube, a reagent disposed within the buffer tube, a nozzle cap, and a test card, the test kit is for testing to obtain a test result of a presence or a non-presence of an infection that utilizes an internet connected electronic device with a camera for communication of said authentication and tracking process to third parties, said medical testing apparatus comprising:
   (a) a test stand that is sized and configured to partially receive the electronic device and to partially receive the test kit in a positional alignment to operationally facilitate the camera to more accurately record an unique identification code for each test kit component, and for the camera to identify user facial recognition, further said test stand records the test kit process steps using the camera including the presence or non-presence of the infection, wherein said test stand further comprises a base mount portion that has a first pivotal attachment to a camera mount portion, wherein said test stand first pivotal attachment is about a first pivotal axis, wherein operationally said test stand camera mount portion in a test stand second operational state facilitates the electronic device and its camera to vertically face the user as said camera mount portion is substantially perpendicular to said base mount portion, wherein said test stand further comprises a spacer base portion that is disposed between said camera mount portion and said base mount portion wherein a second pivotal attachment about a second pivotal axis is disposed between said base mount portion and said spacer base portion, wherein operationally said second pivotal attachment operationally facilitates the electronic device and its camera to pivot to face toward said base mount portion at a selected distance that is between said first and second pivotal axes to enable the camera to operationally video document the test card test results.

2. A medical testing apparatus according to claim 1 wherein said test stand camera mount portion further comprises a compression clamp, a back support portion, and a bottom support portion, wherein said compression clamp, said back support portion, and said bottom support portion are operational to position and support the electronic device camera for the authentication, tracking the test process, and the test result correctly, further to provide a support for suspending the electronic device camera over said base mount portion to video the test result from the test card.

3. A medical testing apparatus according to claim 2 wherein said test stand base mount portion further comprises a deep cavity having a first perimeter with a partial end extension to partially receive the test kit including for the separable components being the extended nasal/oral swab, the buffer tube, and the test card for the operational purpose of positionally locating the unique identification codes on the test kit components of the extended nasal/oral swab, the buffer tube, and a test card for the camera to record.

4. A medical testing apparatus according to claim 3 wherein said test stand base mount portion further comprises a shallow cavity having a second perimeter with said partial end extension to partially receive the test kit card for the operational purpose of positionally locating the unique identification code on the test card and test result on the test card for the camera to record, wherein said shallow cavity is shallow in relation to said deep cavity and said second perimeter is greater than said first perimeter, further wherein said first and second perimeters partially both have a shared perimeter adjacent to said partial end extension.

5. A medical testing apparatus according to claim 4 further comprising a user interface application on the electronic device that is received into said test stand, wherein said user interface application operationally facilitates a camera video dynamic and continuous documenting of the user including the user's identification, tracking the test kit process steps that include placing the test kit into a base mount portion of said test stand for the electronic device camera to scan the identification codes for each of the test kit components that include the extended nasal/oral swab, the buffer tube with reagent disposed within the buffer tube, the nozzle cap, and the test card, while simultaneously verifying the user identity, next verifying the test kit process starting with the step of insertion of the nasal or oral swab by the user to obtain a nasal secretion or saliva on the swab, a next step of inserting of the nasal or oral swab into the extraction buffer tube with the swab disposed in the reagent with rotating agitation of the nasal or oral/swab in the reagent, a further step of removing the nasal/oral swab from the extraction buffer tube while compressing the extraction buffer tube to squeegee the nasal/oral swab into the extraction buffer tube thus creating a nasal section fluid mix or a saliva fluid mix, a continuing step of placing the nozzle cap onto the extraction buffer tube, a next step of placing the test card flat to be specifically positionally received into said base mount portion of said test stand then applying drops of the nasal section fluid mix or saliva fluid mix into a specimen well of the test card and initiating pivotal movement of a camera mount portion of said test stand of about ninety degrees to align the camera to verify the test results of the presence or non-presence of an infection as indicated by the test card after a selected period of time, wherein the test results, user authentication, and verification of the test process steps are further communicated to an internet portal for a third party to have access to the test result, user authentication, and verification of the test process steps.

6. A medical testing apparatus for helping to authenticate and track the process of collecting test samples from a separate test kit that is received partially into said medical test apparatus wherein the test kit that includes components of an extended nasal/oral swab, a buffer tube, a reagent disposed within the buffer tube, and a nozzle cap, said medical testing apparatus documenting the transfer of the test sample to a remote laboratory that will determine the presence or non-presence of an infection, wherein said medical testing apparatus utilizes an internet connected electronic device with a camera for communication of said authentication and tracking process to the remote laboratory, wherein the internet connected device conveys the presence or non-presence of the infection from the remote laboratory to said medical testing apparatus, said medical testing apparatus comprising:
(a) a test stand that is sized and configured to partially receive the electronic device and to partially receive the test kit in a positional alignment to operationally facilitate the camera to more accurately record an unique identification code for each test kit component, and for the camera to identify user facial recognition, further said test stand records the test kit process steps of collecting samples using the camera, wherein said test stand further comprises a base mount portion that has a first pivotal attachment to a camera mount portion, wherein said test stand first pivotal attachment is about a first pivotal axis, wherein operationally said test stand camera mount portion in a test stand second operational state facilitates the electronic device and its camera to vertically face the user as said camera mount portion is perpendicular to said base mount portion, wherein said test stand further comprises a spacer base portion that is disposed between said camera mount portion and said base mount portion wherein a second pivotal attachment about a second pivotal axis is disposed between said base mount portion and said spacer base portion, wherein operationally said spacer base portion facilitates the electronic device and its camera to be at a selected distance from said base mount portion that partially receives the test kit in a positional alignment to better operationally facilitate the camera to more accurately record the unique identification code for the test kit components, and for the camera to identify user facial recognition, further said test stand records the test kit process steps of collecting samples using the camera.

7. A medical testing apparatus according to claim 6 wherein said test stand camera mount portion further comprises a compression clamp, a back support portion, and a bottom support portion, wherein said compression clamp, said back support portion, and said bottom support portion are operational to better secure the electronic device camera positional alignment to operationally facilitate the camera to more accurately record the unique identification code for the test kit components, and for the camera to identify user facial recognition, further said test stand records the test kit process steps of collecting samples using the camera.

8. A medical testing apparatus according to claim 7 wherein said test stand base mount portion further comprises a deep cavity having a first perimeter with a partial end extension to partially receive the test kit including for the separable components being the extended nasal/oral swab and the buffer tube, for the operational purpose of positionally locating the unique identification codes on the test kit components of the extended nasal/oral swab and the buffer tube for the camera to record.

9. A medical testing apparatus according to claim 8 further comprising a user interface application on the electronic device that is received into said test stand, wherein said user interface application operationally facilitates a camera video dynamic and continuous documenting of the user including the user's identification, tracking the test kit process steps that include placing the test kit into a base mount portion of said test stand for the electronic device camera to scan identification codes for each of the test kit components that include the extended nasal/oral swab, the buffer tube with reagent disposed within the buffer tube, and the nozzle cap, while simultaneously verifying the user identity, next verifying the test kit process starting with the step of insertion of the nasal or oral swab by the user to obtain a nasal secretion or saliva on the swab, a next step of inserting of the nasal or oral swab into the extraction buffer tube with the swab disposed in the reagent with rotating agitation of the nasal or oral/swab in the reagent, a further step of removing the nasal/oral swab from the extraction buffer tube while compressing the extraction buffer tube to squeegee the nasal/oral swab into the extraction buffer tube thus creating a nasal/oral section fluid mix, a continuing step of placing the nozzle cap onto the extraction buffer tube, a further step of placing the nozzle cap and extraction buffer tube assembly into an envelope that is sealed with an envelope scan code, wherein the envelope is sent to an outside laboratory for obtaining the test result, wherein the test user authentication and verification of the test process steps are further communicated to an internet portal for a third party to have access to the user authentication and verification of the test process sample collection steps.

10. A medical testing apparatus for a user to help to authenticate and track the process of obtaining a test result of a presence or a non-presence of an infection that utilizes an internet connected electronic device with a camera for communication of said authentication and tracking process to third parties, said medical testing apparatus comprising:
 (a) a test kit that includes components each having an unique identification code, wherein said components include an extended nasal/oral swab, a buffer tube, a reagent disposed within the buffer tube, a nozzle cap, and a test card; and
 (b) a test stand that is sized and configured to partially receive the electronic device and to partially receive the test kit in a positional alignment to operationally facilitate the camera to more accurately record an unique identification code for each component of the test kit, and for the camera to identify user facial recognition, further said test stand records the test kit process steps using the camera including the presence or non-presence of the infection, wherein said test stand further comprises a base mount portion that has a first pivotal attachment to a camera mount portion, wherein said test stand first pivotal attachment is about a first pivotal axis, wherein operationally said test stand camera mount portion in a test stand second operational state facilitates the electronic device and its camera to vertically face the user as said camera mount portion is perpendicular to said base mount portion, wherein said test stand further comprises a spacer base portion that is disposed between said camera mount portion and said base mount portion wherein a second pivotal attachment about a second pivotal axis is disposed between said base mount portion and said spacer base portion, wherein operationally said second pivotal attachment facilitates the electronic device and its camera to pivot to face toward said base mount portion at a selected distance that is between said first and second pivotal axes to enable the camera to video document said test card test results.

11. A medical testing apparatus according to claim 10 wherein said test stand camera mount portion further comprises a compression clamp, a back support portion, and a bottom support portion, wherein said compression clamp, said back support portion, and said bottom support portion are operation to position the electronic device camera for the authentication, tracking the test process, and the test result correctly, further to provide a support for suspending the electronic device camera over said base mount portion to video the test result from said test card.

12. A medical testing apparatus according to claim 11 wherein said test stand base mount portion further comprises a deep cavity having a first perimeter with a partial end extension to partially receive the test kit including for separable components being said extended nasal/oral swab, said buffer tube, and said test card for the operational purpose of positionally locating said unique identification codes on said components of said extended nasal/oral swab, said buffer tube, and said test card for the camera to record.

13. A medical testing apparatus according to claim 12 wherein said test stand base mount portion further comprises a shallow cavity having a second perimeter with said partial end extension to partially receive said test kit card for the operational purpose of positionally locating said unique identification code on said test card and test result on said test card for the camera to record, wherein said shallow cavity is shallow in relation to said deep cavity and said second perimeter is greater than said first perimeter, further wherein said first and second perimeters partially both have a shared perimeter.

14. A medical testing apparatus according to claim 13 further comprising a user interface application on the electronic device that is received into said test stand, wherein said user interface application operationally facilitates a camera video dynamic and continuous documenting of the user including the user's identification, tracking said test kit process steps that include placing said test kit into a base mount portion of said test stand for the electronic device camera to scan identification codes for each of said test kit components that include said extended nasal/oral swab, said buffer tube with reagent disposed within said buffer tube, said nozzle cap, and said test card, while simultaneously verifying the user identity, next verifying said test kit process starting with the step of insertion of said nasal or oral swab by the user to obtain a nasal secretion or saliva on said swab, a next step of inserting of said nasal or oral swab into said extraction buffer tube with said swab disposed in said reagent with rotating agitation of said nasal or oral/swab in said reagent, a further step of removing said nasal/oral swab from said extraction buffer tube while compressing said extraction buffer tube to squeegee said nasal/oral swab into said extraction buffer tube thus creating a nasal section fluid mix or a saliva fluid mix, a continuing step of placing said nozzle cap onto said extraction buffer tube, a next step of placing said test card flat to be specifically positionally received into said base mount portion of said test stand then applying drops of said nasal section fluid mix or saliva fluid mix into a specimen well of said test card and initiating pivotal movement of a camera mount portion of said test stand of about ninety degrees to align the camera to verify the test results of the presence or non-presence of an infection as indicated by said test card after a selected period of time, wherein the test results, user authentication, and verification of the test process steps are further communicated to an internet portal for a third party to have access to the test result, user authentication, and verification of the test process steps.

\* \* \* \* \*